(12) United States Patent
Wang et al.

(10) Patent No.: US 11,426,568 B2
(45) Date of Patent: Aug. 30, 2022

(54) APPLICATORS FOR TREATING VAGINAL DRYNESS

(71) Applicant: The Procter & Gamble Company, Cincinnati, OH (US)

(72) Inventors: Samantha Chen-Yee Wang, Cincinnati, OH (US); Nery Vanesa Breslin, Hamilton, OH (US); Kyra L Wilsonhouck, Cincinnati, OH (US)

(73) Assignee: THE PROCTER & GAMBLE COMPANY, Cincinnati, OH (US)

(*) Notice: Subject to any disclaimer, the term of this patent is extended or adjusted under 35 U.S.C. 154(b) by 494 days.

(21) Appl. No.: 16/257,151

(22) Filed: Jan. 25, 2019

(65) Prior Publication Data

US 2019/0231683 A1  Aug. 1, 2019

Related U.S. Application Data

(60) Provisional application No. 62/683,126, filed on Jun. 11, 2018, provisional application No. 62/622,289, (Continued)

(51) Int. Cl.
| | | |
|---|---|---|
| *A61M 35/00* | (2006.01) | |
| *A61F 2/00* | (2006.01) | |
| *A61K 9/00* | (2006.01) | |
| *A61K 9/06* | (2006.01) | |
| *A61M 31/00* | (2006.01) | |
| *A61K 9/02* | (2006.01) | |
| *A61K 36/286* | (2006.01) | |
| *A61K 36/88* | (2006.01) | |

(52) U.S. Cl.
CPC ........... *A61M 35/00* (2013.01); *A61F 2/0095* (2013.01); *A61K 9/0034* (2013.01); *A61K 9/06* (2013.01); *A61M 31/00* (2013.01); *A61K 9/02* (2013.01); *A61K 36/286* (2013.01); *A61K 36/88* (2013.01); *A61M 2210/1475* (2013.01)

(58) Field of Classification Search
CPC .......... A61M 31/00; A61M 2210/1475; A61M 2210/1483; A61M 35/00; A61K 9/0034; A61K 9/06; A61K 9/02; A61K 36/286; A61K 36/88
See application file for complete search history.

(56) References Cited

U.S. PATENT DOCUMENTS

2002/0161313 A1* 10/2002 Sak ..................... A61B 10/0045
600/569
2005/0282835 A1* 12/2005 Villanueva ........... A61K 31/355
514/267
(Continued)

FOREIGN PATENT DOCUMENTS

CN          106345045 A       1/2017

OTHER PUBLICATIONS

Shah, P., Shit, S.C., A Review on Silicone Rubber. Natl. Acad. Sci. Lett. 36, 355-365 (2013). https://doi.org/10.1007/s40009-013-0150-2 (Year: 2013).*
(Continued)

*Primary Examiner* — James D Ponton
(74) *Attorney, Agent, or Firm* — Melissa G. Krasovec

(57) ABSTRACT

A kit for treating vaginal dryness is provided. The kit comprises a hand held applicator and a dispenser or receptacle storing a vaginal care composition.

19 Claims, 16 Drawing Sheets

Related U.S. Application Data filed on Jan. 26, 2018, provisional application No. 62/622,298, filed on Jan. 26, 2018, provisional application No. 62/622,280, filed on Jan. 26, 2018.

(56) References Cited

U.S. PATENT DOCUMENTS

| | | | |
|---|---|---|---|
| 2006/0011666 A1* | 1/2006 | Wurtz | B65D 1/095 |
| | | | 222/541.1 |
| 2006/0079924 A1* | 4/2006 | Sanders | A61B 1/32 |
| | | | 606/192 |
| 2006/0122563 A1 | 6/2006 | Ziv | |
| 2007/0062517 A1* | 3/2007 | Barker | A61M 11/007 |
| | | | 128/200.14 |
| 2009/0095304 A1* | 4/2009 | Richardson | A61F 2/0009 |
| | | | 128/834 |
| 2014/0155840 A1* | 6/2014 | Tseng | A61M 31/00 |
| | | | 604/257 |
| 2015/0148720 A1* | 5/2015 | Harmon | A61H 19/30 |
| | | | 601/70 |
| 2017/0165411 A1 | 6/2017 | Peters | |

OTHER PUBLICATIONS

Search Report; PCT/US2019/015149; dated May 3, 2019; 14 Pages.

* cited by examiner

APPLICATORS FOR TREATING VAGINAL DRYNESS

TECHNICAL FIELD

The present disclosure generally relates to applicators for treating vaginal dryness, and more specifically to applicators for administering a composition to facilitate the treatment of vaginal dryness, as well as kits and methods thereof.

BACKGROUND

Estimates indicate that by 2030 there will be about 1.2 billion menopausal and post-menopausal women in the world. Given that the average age at which menopause occurs has remained the same and that life expectancy among women has generally increased, the number of post-menopausal women is expected to grow. As such, there is increasing concern surrounding the conditions and symptoms experienced by perimenopausal, menopausal, post-menopausal women, and the need for treatment therefore is growing as well.

Menopause generally occurs 12 months after a woman's last menstrual period; however, it is considered a gradual process. As is well known, menopause may be accompanied by hot flashes, night sweats, mood changes, stress, fatigue, irritability, and difficulty with memory. Furthermore, menopause is associated with a decrease in estrogen production. Decreased estrogen levels may result in changes to both the internal and external genitalia, including vaginal atrophy and a thinning of the vaginal and urethral mucous membrane, a loss in vaginal elasticity, and a reduction in gland secretion, which may be accompanied by a decrease in tissue hydration. Some estimate that up to 57% of perimenopausal and post-menopausal woman suffer from vaginal atrophy. Vaginal atrophy can facilitate urogenital infections and may also result in vaginal irritation, burning, dryness, itching, odor, and pain during sexual intercourse (dyspareunia), thus, greatly impacting a woman's quality of life. For example, women may experience feelings of isolation, fear, resignation, anger, and a loss of libido and intimacy as a result. In addition to menopause, women may also experience a drop in estrogen levels or fluctuating hormones during breastfeeding, breast cancer hormonal treatment, and after surgical removal of the ovaries, pelvic radiation therapy for cancer, and chemotherapy.

There are a variety of solutions that have been proposed to address the above-described vaginal conditions and symptoms. Prescription-based remedies have included hormone replacement therapy, which can include an estrogen supplement with or without progesterone. In some instances, the hormonal therapies may be applied deep within the vaginal canal by plunger type applicators. For example, creams may be dispensed into the vaginal canal by a plunger type applicator (e.g., Premarin®, available from Pfizer, Inc. is supplied with a plunger type applicator for dispensing the cream into the vaginal canal; and Estrace®, available from Allergan, Inc., also is supplied with a plunger type applicator), tablets may be similarly placed deep into the vaginal canal by a plunger type applicator (e.g., Vagifem®, available from Novo Nordisk Health Care AG, is supplied with an applicator to place a tablet within the vaginal canal, or Intrarosa, available from Endoceutics, Inc., is supplied with a plunger type applicator to place inserts into the vaginal canal) or insertable rings (e.g., Estring®, available from Pfizer, Inc., which is likewise inserted into the vaginal canal).

While hormonal therapies have shown positive effects in the treatment of vaginal atrophy, some women continue to experience the symptoms, and for many women, such treatment can prove to be too expensive. Hormone replacement therapy has also been reduced by contraindications such as a history of cancer and thromboembolism. Moreover, due to the nature of the condition, women may feel uncomfortable and/or embarrassed discussing the above-described symptoms and may avoid seeking a doctor's consultation. Additionally, many women stop annual visits to gynecologists, leaving their primary care family physician as the main resource, yet few primary care physicians address or treat menopausal symptoms since menopause is viewed as a "natural" process.

There are also several over-the-counter solutions that have been offered to consumers to treat various symptoms and/or conditions experienced by women. These include vaginal moisturizers (e.g., Replens® Long Lasting Moisturizer and Replens® Moisture Restore External Comfort Gel, or HyaloGyn/HyaloFemme, available from Fidia Farmaceutici SpA and both supplied with disposable applicators to place in the vaginal canal), lubricants for reducing discomfort during intimacy (e.g., Replens® Silky Smooth Personal Lubricant, Astroglide®, K-Y® gels and lubricants), wipes (e.g., Vagisil® Anti-Itch Medicated Wipes), sprays, and washes and douches for eliminating bacteria that can cause unpleasant odors (e.g., Summer's Eve®). The Replens® Long Lasting Moisturizer, available from Church & Dwight, Inc., is provided with a plunger type applicator for depositing the moisturizer within the vaginal canal. The makers of Replens® have published a number of studies regarding the benefits of using the Replens® Long Lasting Moisturizer (see, e.g., https://www.womenshealthcaresolutions.com/clinical-studies/replens/).

While the aforementioned over-the-counter solutions may be useful, some forms may not prioritize women's intimate health or the usage experience. For example, generally, moisturizers do not provide a desired lubricity, and typically, lubricants may not have a long-lasting effect. The methods of application (e.g., digitally—using one's own fingers) and marketing aesthetics (e.g., as adjuncts to sex) can also serve as barriers to women seeking treatment. Additionally, plunger type applicators for delivering a composition deeper within the vaginal canal may be an added irritant, may appear intimidating and may compromise the fragile tissue.

There are opportunities for improvement. For example, it would be advantageous to provide applicators for treating vaginal dryness by treating the vaginal introitus, as well as, optionally, the vulva, vestibule, labia majora, labia minora, and/or external urogenital tract but not deeper within the vaginal canal. It would be advantageous to provide an applicator having an applicator that is comfortable for use in these anatomical areas, enables spreading of a vaginal care composition to these anatomical areas, is hygienic, is ergonomic, has a non-intimidating shape (e.g., a non-phallic) and size, is discrete (e.g., can be easily carried in a purse or other bag) and protects fingers from soiling during use. It would be advantageous to provide an applicator that is easily usable and/or manipulatable by a female user while in a variety of positions (e.g., standing, seated or laying down) even if the female user is unable to directly observe the vaginal tissues of interest during use. It would be advantageous to provide an applicator that appears less like a medicinal or sexual device and more like a beauty care inspired device that provides a delightful usage experience and encourages long term habit adoption by a female user. It would be advantageous to provide a kit having a vaginal care composition for use with such applicators and a dispenser or receptacle for storing such compositions. It would also be advantageous to provide a method of using a vaginal care composition with such applicators and a dispenser or receptacle for storing such compositions. While numerous opportunities for improvement are described above, it will be appreciated that the disclosure hereafter is not limited to providing any or all such improvements.

SUMMARY

The present disclosure relates to a hand held applicator for treating vaginal dryness, where the applicator comprises a non-electrical, elongate body for applying a vaginal care composition, where the body comprises a proximal end, a cone-shaped insertion portion having a tip opposite the proximal end, a grippable portion comprising a texture disposed adjacent the proximal end, and where the applicator has an overall length L1 from about 20 mm to 90 mm and a maximum width $W_{max}$ from about 20 mm to about 80 mm.

The present disclosure also relates to a method for treating vaginal dryness comprising a female user suffering from vaginal dryness grasping an applicator, the female user depositing an amount of a vaginal care composition on at least a portion of the outer surface of the applicator, the female user administering at least a portion of the amount of the vaginal care composition to her vaginal introitus, where administering the vaginal care composition includes inserting the applicator into her vaginal introitus a distance of about 25 mm or less.

The present disclosure also relates to a kit for treating vaginal dryness comprising (i) a dispenser or receptacle storing a vaginal care composition comprising one or more of an oil in water emulsion, an estrogen agent, or a progesterone agent; and (ii) a non-electrical, hand-held applicator separate from the dispenser or receptacle, where the applicator comprises an elongate body having a longitudinal axis, a proximal end and a tapered insertion portion having a tip opposite the proximal end, the applicator having an overall length L1 from about 20 mm to 90 mm and a maximum width $W_{max}$ from about 20 mm to about 80 mm.

BRIEF DESCRIPTION OF THE DRAWINGS

The above-mentioned and other features and advantages of the present disclosure, and the manner of attaining them, will become more apparent and the disclosure itself will be better understood by reference to the following description of non-limiting embodiments of the disclosure taken in conjunction with the accompanying drawings, wherein.

Figure 1:
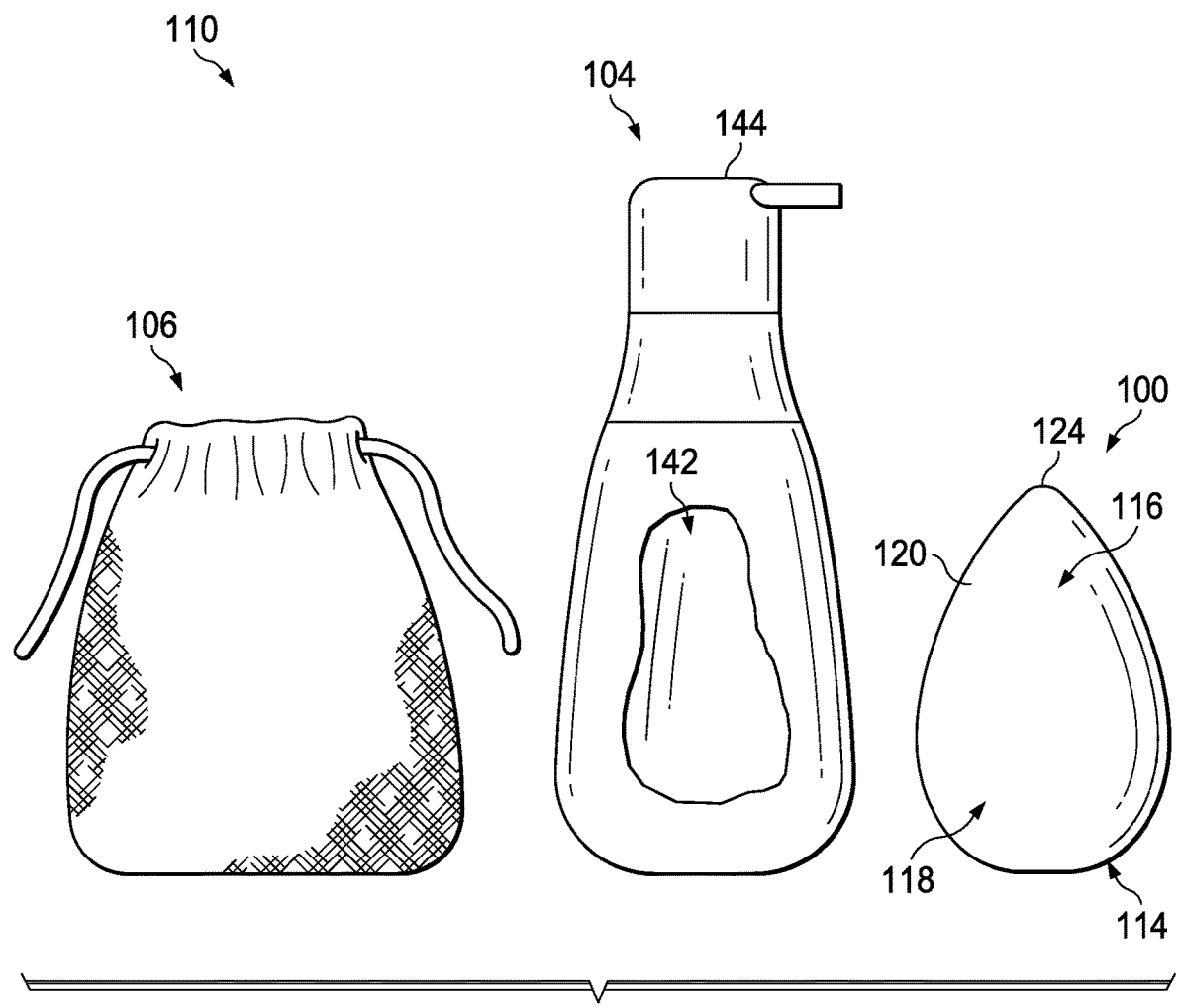
FIG. 1 is a front view of one example of a kit, including a pouch, a dispenser for a vaginal care composition, and one example of a hand-held applicator.

Other features and advantages of the invention will be apparent from the following detailed description and from the claims.

DETAILED DESCRIPTION

Various non-limiting embodiments of the present disclosure will now be described to provide an overall understanding of the principles of the function, design and use of the applicators, compositions, kits and methods disclosed herein. One or more examples of these non-limiting embodiments are illustrated in the accompanying drawings. Those of ordinary skill in the art will understand that the embodiments and methods described herein and illustrated in the accompanying drawings are non-limiting example embodiments and that the scope of the present disclosure is defined solely by the claims. The features illustrated or described in connection with one non-limiting embodiment can be combined with the features of other non-limiting embodiments. Such modifications and variations are intended to be included within the scope of the present disclosure.

All percentages are by weight of the vaginal care composition, unless specifically stated otherwise. All ratios are weight ratios, unless specifically stated otherwise. All ranges are inclusive of narrower ranges and combinable. Delineated upper and lower range limits are interchangeable to create further ranges not explicitly delineated. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity.

The compositions of the disclosure can comprise, consist essentially of, or consist of, the components as wen as optional ingredients described herein. As used herein, "consisting essentially of means that the applicator, composition or component may include additional ingredients or features, but only if the additional ingredients or features do not materially alter the basic and novel characteristics of the claimed applicators, compositions or methods. As used in the description and the appended claims, the singular forms "a," "an", and "the" are intended to include the plural forms as well, unless the context clearly indicates otherwise. Unless otherwise defined, all technical and scientific terms used herein have the same meaning as commonly understood by one of ordinary skill in the art to which this invention belongs.

"Cross-linked silicone rubber" means an elastomeric solid material resulting from cross-linking (e.g., sometimes referred to as "curing") a liquid silicone rubber. Cross-linking of a liquid silicone rubber can occur by any process or means known in the art, including, but not limited to, cross-linking by addition (e.g., platinum), cross-linking by condensation or cross-linking with radicals (e.g., peroxide). Cross-linking may be facilitated by a cross-linking agent or temperature.

"Estrogen agent" means any natural or synthetic estrogen hormone (e.g., estrone, estradiol and estriol), metabolites thereof, esters thereof, analogues thereof, phytoestrogens (e.g., isoflavones, coumestans, prenylflavonoids), estrogen precursors (e.g., dehydroepiandrosterone) and/or any compound which binds to an estrogen receptor or which otherwise exhibits at least mild or weak estrogen-like effects, including selective estrogen receptor modulators ("SERM") such as, for example: afimoxifene (4-hydroxytamoxifen), arzoxifene, bazedoxifene, clomifene, femarelle (Dr1756a), lasofoxifene, ormeloxifene, raloxifene, tamoxifen, toremifene, mifepristone (RU486), VA2914, ulipristal, Proellex, Asoprisnil, and CDB-4124.

"Grippable portion" means a portion having an outer shape and size which may be grasped by 2 or more fingertips of a human hand to manipulate the applicator in use.

"Integrally constructed" and "integrally formed" mean broadly a structure or feature formed from two or more materials, pieces and/or parts that are not easily disassembled. In some embodiments, the materials, pieces and/or parts may be bonded (e.g., chemical, thermal or adhesive) or mechanically fastened together (e.g., inter-molded parts, interlocking parts). Some non-limiting manufacturing processes useful for forming the foregoing include injection molding, casting, bonding and printing processes.

"Liquid silicone rubber" means a cross-linkable liquid comprising a siloxane or silicone polymer (e.g., polysiloxanes, polydimethylsiloxanes (PDMS) and combinations thereof).

"Medical grade" means a material that passes either i) one or more of the United States Pharmacopeia and National Formulary (USP-NF) Class IV, V and Class VI designations, or ii) ISO 10993 testing for one or more of cytotoxicity (ISO 10993-5), 7-day implant (ISO 10993-6), skin irritation (ISO 10993-10) and skin sensitization (ISO 10993-10).

"Micro-texture" means a texture or surface finish having a surface texture, Sq, from about 3 µm to about 30 µm, or from about 3.3 µm to about 20 µm, or from about 3.5 µm to about 10 µm as measured by the Surface Texture Procedure below.

"Perimenopausal" woman is one who in the absence of hormone replacement therapy or other medication would experience a change in her intermenstrual cycle interval and have associated symptoms of estrogen deficiency, such as vasomotor flushes, vaginal dryness and/or worsening premenstrual syndrome. Also included are women who in the absence of hormone replacement therapy or other medication would experience less than 12 months amenorrhea.

"Pharmacologically effective amount", "therapeutically effective amount" or simply "effective amount" means the amount of a composition, or ingredient thereof, effective to produce the intended pharmacological, therapeutic or preventive result.

"Postmenopausal" woman is one who in the absence of hormone replacement therapy or other medication would experience at least 12 months of amenorrhea.

"Progesterone agent" means any natural or synthetic progesterone hormone, metabolites thereof, analogues thereof, progesterone precursors and/or any compound which binds to a progesterone receptor or which otherwise exhibits at least mild or weak progesterone-like effects, including selective progesterone receptor modulators ("SPRM") such as, for example, telapristone.

"Rotational symmetry" means the applicator, or a portion thereof such as the insertion portion or the grippable portion, has an overall shape that looks the same thru some rotation (e.g., 45°, 90°, 135°, 180°, 225°, 270°, 315°, or 360° about its longitudinal axis. For example, an applicator that has an overall shape that looks the same thru a rotation of 45° is considered rotationally symmetrical thru that 45° rotation. Likewise, an applicator that has an overall shape that looks the same thru one full rotation is considered rotationally symmetrical thru 360°. The reference to rotational symmetry herein, unless stated otherwise, ignores surface features such as print, coloring, coatings, text, graphics, dosing indicators, insertion indicators, surface textures and surface finishes.

"Smooth" means a surface having a surface texture, Sq, less than about 30 µm, or less than about 10 µm, or less than about 3 µm as measured by the Surface Texture Procedure below. Smooth surfaces include surfaces having a micro-texture.

"Substantially free" means a component or material is present in amount less than 0.1%, 0.05%, 0.025%, 0.01%, or 0.001% by weight of the vaginal care composition.

"Taper" means to become smaller toward one end. An applicator, or feature thereof such as the insertion portion, may have a taper that is gradual, substantial, intermittent, continuous and combinations thereof. For example, an applicator is considered to taper from the maximum width to the tip merely if the bulk cross-sectional area (e.g., inclusive of both solid cross-sectional area and void cross-sectional area) at the tip is less than the bulk cross-sectional area at the maximum width, even though, for example, the bulk cross-sectional area may intermittently increase or remain constant between the maximum width and the tip. Some non-limiting examples of tapered insertion portions are shown in FIGS. 5A to 5G. A continuous taper is a taper wherein the bulk cross-sectional area of the applicator decreases along at least 80%, 90%, 95% or 100% of a traversal from a first point on the longitudinal axis to a second point on the longitudinal axis of the applicator (e.g., from $W_{max}$ to the tip). Some non-limiting examples of a continuous taper are shown in FIGS. 5A to 5G.

"Vaginal care composition" means any composition that is suitable for application to the vaginal introitus and/or one or more of the vulva, vestibule, labia majora, labia minora, and/or external urogenital tract and which is useful for treating or ameliorating vaginal dryness.

A. Desirability of Treating the Vaginal Introitus and External Vaginal Tissues i. Female Use and Deprivation Study Applicant conducted a blinded and instructed, daily, single product use test over a 4-week time period followed by a follow-up 2-week deprivation assessment. Participants were post-menopausal (1-15 years) women who were sexually active and experienced dryness on a regular basis. In one run of the test (Leg 1), the participants (N=22) applied a daily 1 g dosage of the composition set forth in Table 1 using a plunger-type applicator. In another run of the test (Leg 2), the participants (N=22) applied a daily 1 g dose of the composition set forth in Table 1 to the distal part of the vagina (vaginal opening, also referred to as the vaginal introitus) and the inner labia using their fingers. Prior to starting the study, the participants had a minimum 3-day abstinence from their then current vaginal care routine and were instructed to refrain from using these products (e.g., douches, lubricants, moisturizers, sprays, etc.) for the duration of the study. The participants completed a questionnaire following the 3-day abstinence period, the questionnaire following 2 weeks of product usage, the questionnaire following 4 weeks of product usage, and a deprivation questionnaire 6 weeks after the start of the study (i.e., 2 weeks following last product usage).

TABLE 1

Composition Formulation for Testing

| Ingredient | Amount (%) |
| --- | --- |
| Water | 73.38 |
| Sodium Hyaluronate | 0.5 |
| Olus Oil and Camelina Sativa Seed Oil | 0.5 |
| Niacinamide | 3 |
| Glycerin | 10 |
| Stearyl Dimethicone | 1 |
| Disodium EDTA | 0.1 |
| Tocopheryl Acetate | 0.5 |
| Polymethylsilsesquioxane | 0.25 |
| Cetearyl Glucoside, Cetearyl Alcohol | 0.2 |
| Behenyl Alcohol | 0.8 |
| Geogard ® ECT (81.5% Benzyl Alcohol, 11.5% Salicylic Acid, 4.5% Glycerin, 2.5% Sorbic Acid) | 1 |
| Cetyl Alcohol | 0.64 |
| Stearyl Alcohol | 0.96 |
| PEG-100 Stearate | 0.1 |
| Polyacrylamide(and)C13-14 Isoparaffin(and)Laureth-7 | 3 |
| Panthenol | 1 |
| Citric Acid | 0.48 |
| Sodium Citrate | 0.59 |
| Dimethicone and Dimethiconol | 2 |

The questions and statistical summaries of the results of the questionnaire are set forth in Table 2-4. Participants answered questions on the perceived severity of vaginal dryness (Table 2) and discomfort/pain with intercourse (Table 3), thinking of the past 7 days, as none, mild, moderate or severe. The tables include the p-values for week 2 and week 4 compared to baseline, and deprivation-week 6 compared to baseline. Both methods of application showed perceived improvements after two weeks of daily use (p-values<0.001). Two weeks of deprivation from product use showed that perceived benefits are reduced and ratings move back toward the baseline. Thus, it is presently believed that a deep vaginal applicator may not be necessary to achieve important benefits.

TABLE 2

Vaginal Dryness: self-evaluation (past 7 days)

| Treatment | None | Mild | Moderate | Severe | Comparison to Baseline p-value |
| --- | --- | --- | --- | --- | --- |
| Baseline | | | | | |
| Leg 1 | 0 (0%) | 5 (24%) | 10 (48%) | 6 (29%) | |
| Leg 2 | 0 (0%) | 4 (18%) | 13 (59%) | 5 (23%) | |
| Week 2 | | | | | |
| Leg 1 | 9 (43%) | 10 (48%) | 2 (10%) | 0 (0%) | <.0001 |
| Leg 2 | 8 (36%) | 14 (64%) | 0 (0%) | 0 (0%) | <.0001 |
| Week 4 | | | | | |
| Leg 1 | 13 (68%) | 6 (32%) | 0 (0%) | 0 (0%) | <.0001 |
| Leg 2 | 16 (73%) | 5 (23%) | 1 (5%) | 0 (0%) | <.0001 |
| Week 6-Deprivation | | | | | |
| Leg 1 | 1 (5%) | 10 (50%) | 7 (35%) | 2 (10%) | 0.0267 |
| Leg 2 | 2 (9%) | 10 (45%) | 8 (36%) | 2 (9%) | 0.0121 |

TABLE 3

Discomfort/Pain with Sexual Intercourse: (past 7 days)

| Treatment | None | Mild | Moderate | Severe | Comparison to Baseline p-value |
| --- | --- | --- | --- | --- | --- |
| Baseline | | | | | |
| Leg 1 | 0 (0%) | 6 (29%) | 7 (33%) | 8 (38%) | |
| Leg 2 | 1 (5%) | 5 (23%) | 12 (55%) | 4 (18%) | |
| Week 2 | | | | | |
| Leg 1 | 9 (43%) | 10 (48%) | 2 (10%) | 0 (0%) | <.0001 |
| Leg 2 | 11 (50%) | 10 (45%) | 1 (5%) | 0 (0%) | <.0001 |

TABLE 3-continued

Discomfort/Pain with Sexual Intercourse: (past 7 days)

| Treatment | None | Mild | Moderate | Severe | Comparison to Baseline p-value |
|---|---|---|---|---|---|
| Week 4 | | | | | |
| Leg 1 | 10 (53%) | 9 (47%) | 0 (0%) | 0 (0%) | <.0001 |
| Leg 2 | 14 (64%) | 7 (32%) | 1 (5%) | 0 (0%) | <.0001 |
| Week 6-Deprivation | | | | | |
| Leg 1 | 1 (5%) | 12 (60%) | 5 (25%) | 2 (10%) | 0.0096 |
| Leg 2 | 6 (27%) | 8 (36%) | 4 (18%) | 4 (18%) | 0.0442 |

In this study, panelists also answered questions regarding their physical and emotional status (Table 4). Participants answered questions as Not At All Satisfied (1) to Extremely Satisfied (5). The tables also include the p-values for week 4 compared to baseline and deprivation-week 6 compared to baseline. Both methods of application showed perceived improvements after four weeks of daily use (p-values<0.001) on physical descriptors such as the internal and external natural lubrication questions. It is presently believed that additional benefits may be realized by including application of a composition to the vaginal introitus and on the external vaginal tissue as opposed to only internally or deeper within the vaginal canal.

(fourchette) and labia majora and processed for histology (H&E staining and CD3 immunohistochemistry) and transcriptomic analyses. Other data collected included self-assessed symptoms, blood estradiol, testosterone, and serum hormone binding globulin (SHBG), and the pH of the labia majora. The results indicate that the introitus appears exquisitely sensitive to menopause/hormone therapy status. Dramatic changes were observed by histology (H&E) and by transcriptomics, including a thinning of the epithelium in post-menopausal subjects with vaginal atrophy. Furthermore, there was differential expression of many genes likely to contribute to tissue remodeling in the atrophic introitus. Levels of expression of genes associated with wounding, angiogenesis, cell migration/locomotion, dermal structure, apoptosis, inflammation, epithelial cell differentiation, and fatty acid, carbohydrate, and steroid metabolism were significantly different comparing atrophied to normal introitus. While changes were also observed at the labia, that site appeared less sensitive to menopause/hormone therapy status. The introitus displayed many similarities with the histological and transcriptomic changes in the vagina that are associated with atrophy and HT treatment. The results are believed to indicate that the histological and transcriptomic changes occurring within the introitus during menopause likely contribute to the symptom presentation associated with menopause Study Design Three cohorts of ten healthy women each were selected for this study and included (1) pre-menopausal women

TABLE 4

Physical and emotional: self-evaluation (past 7 days)

| Treatment | Feel Confident of Positive Sexual Experience (past 7 days) | Comfortable during Sexual Intercourse (past 7 days) | Feel Vibrant (past 7 days) | Feel Feminine (past 7 days) | Elasticity of My Vagina (past 7 days) | Level of Natural Lubrication in my External Vulva Area (past 7 days) | Level of Natural Lubrication in my Internal Vaginal Area (past 7 days) |
|---|---|---|---|---|---|---|---|
| Baseline | | | | | | | |
| Leg 1 | 2.33 (1.03) | 2.05 (0.87) | 2.56 (0.92) | 2.55 (1.15) | 1.88 (0.78) | 1.44 (0.62) | 1.22 (0.43) |
| Leg 2 | 2.36 (1.29) | 2.00 (1.15) | 2.27 (1.03) | 2.50 (1.22) | 2.36 (1.22) | 1.33 (0.58) | 1.27 (0.55) |
| Week 4 | | | | | | | |
| Leg 1 | 4.06 (1.00) | 3.83 (1.04) | 3.94 (0.80) | 4.00 (0.84) | 3.41 (1.12) | 3.47 (1.26) | 3.58 (1.35) |
| Leg 2 | 4.18 (1.10) | 4.18 (1.10) | 3.95 (0.72) | 4.09 (0.81) | 3.71 (1.19) | 4.14 (0.94) | 4.05 (1.13) |
| Comparison to Baseline (p-value) | | | | | | | |
| Leg 1 | <.0001 | <.0001 | <.0001 | <.0001 | <.0001 | <.0001 | <.0001 |
| Leg 2 | <.0001 | <.0001 | <.0001 | <.0001 | <.0001 | <.0001 | <.0001 |
| Week 6-Deprivation | | | | | | | |
| Leg 1 | 3.21 (0.98) | 3.05 (1.03) | 3.21 (0.85) | 3.21 (0.85) | 2.74 (0.99) | 2.15 (0.99) | 2.15 (1.09) |
| Leg 2 | 2.82 (1.26) | 2.77 (1.41) | 3.14 (0.77) | 3.32 (0.99) | 2.50 (1.30) | 2.43 (1.03) | 2.05 (1.05) |
| Comparison to Baseline (p-value) | | | | | | | |
| Leg 1 | 0.001 | 0.0004 | 0.0113 | 0.0034 | 0.0053 | 0.002 | 0.0007 |
| Leg 2 | 0.0763 | 0.0204 | 0.0002 | 0.0061 | 0.6956 | <.0001 | 0.0002 | ii. Transcriptomic and Histology Analysis

A study was conducted to determine the effect of menopausal and hormone therapy status on the introitus and labia majora at the levels of histology and global gene expression. Three cohorts of women (pre-menopause, post-menopause, and post-menopause+hormone therapy (HT) of ten each, were selected based on the presentation of clinical atrophy and vaginal pH. Biopsies were obtained from the introitus showing little to no sign of clinical urogenital atrophy and having a vaginal pH<5.0 (Pre-M), (2) post-menopausal women showing signs of clinical urogenital atrophy and having a vaginal pH≥5.0 (Post-M), and (3) post-menopausal women on systemic hormone therapy showing little to no sign of clinical urogenital atrophy and having a vaginal pH<5.0 (Post-M+HT). Subjects were examined for severity of attributes associated with atrophy including (a) rugosity at the hymeneal area, (b) vestibule morphology, (c) elasticity (stenosis) at the introitus, (d) patulousness or telescoping urethra, and (e) color (pallor, friability, petechiae). Each attribute was graded on scale of none (0), minimal/mild (1), or marked/severe (2). A collective score≤2 was considered non-atrophic and a score ≥6 was considered atrophic. Vaginal pH was measured. Vulvar pH was obtained using a flathead pH probe (Skincheck HI98109, Hanna Instruments, Ann Arbor, Mich.). The skin surface was cleansed with Betadine® and then anesthetized with lidocaine just under the area to be biopsied. When the anesthetic had numbed the area, the surface was cleansed with alcohol. A Tischler-Morgan™ biopsy punch (Cooper Surgical 64-689, Trumbull, Conn.) was used at the introitus and the midpoint of the labia majora followed by chromic suture closure. This device insured a uniform biopsy thickness. The side of the labia (left or right) selected for the biopsy was randomized. Each biopsy was cut in half across the epithelial-dermal axis. One half was prepared for transcriptomic analysis and the remaining half was prepared for histological examination. Tissue for histology was fixed in 10% neutral buffered formalin and routinely processed and sectioned for H&E and immunohistochemistry. Tissue for transcriptomic analysis was initially placed in RNALater (ThermoFisher Scientific, Waltham, Mass.) and then frozen and processed using standard techniques for RNA extraction, preparation of labelled cRNA and analysis using Affymetrix (Santa Clara, Calif.) GeneTitan® U219 array plates according to the manufacturer's protocols.

Microarray probe set lists from the introitus and labia majora were filtered for the top 70% by maximum mean signal across the groups to remove transcripts that may not be expressed in the sampled tissues. Filtered probe set lists were subject to hierarchical clustering to visualize global patterns. GO term enrichment analysis to identify regulated biological processes was performed using the DAVID Bioinformatics Resources functional annotation clustering tool with Entrez Gene IDs. The top 70% of probe sets based on maximum mean signal values without statistical filtering was used as the reference gene list.

Histology and Transcriptomic Results and Discussion

H&E stained sections of biopsied tissue from the introitus revealed structural changes that were like more distal vaginal biopsies such as the loss of superficial epithelial layers and epithelial thinning. Equally pronounced was the loss of rete ridges or undulations of the epithelial-dermal interface. A quantitative indication of the degree of undulation is the ratio of the lengths of epithelial-dermal interface to epithelial surface measured in histological sections by image analysis. That parameter for the introitus was significantly related to hormone status (Post-M<Pre-M, p=0.049 and Post-M<Post-M+HT, p=0.047, with no significant difference between Pre-M and Post-M+HT). The changes in the labia majora were directional but non-significant (Post-M<Pre-M, p=0.083). CD3+ T-cells were identified in both the introitus and labial majora tissue, and they were present in both the epithelium and dermis. In the introitus, the relative abundance of CD3+ cells tended to be greater in the menopausal cohorts relative to Pre-M cohort (p=0.017 when compared to Post-M+HT and p=0.119 when compared to Post-M), suggesting that HT did not confer a pre-menopausal status. The abundance of CD3+ cells was significantly greater in the introitus than the labia across each of the three cohorts.

From a histological perspective the changes associated with estrogen and atrophic status of the introitus appear more exaggerated than what has been documented for the vagina. In addition to a thinner epithelial layer devoid of superficial cells in the atrophic post-menopausal cohort, there was a dramatic loss of rete ridges. Rete ridges can be viewed as supporting the structural integrity of the epithelium, anchoring it in the connective tissue. Their loss may contribute to mechanical sensitivity and symptoms of dyspareunia. While rete ridges were also reduced in the labia majora, the changes were more modest, suggesting site specific effects of estrogen.

There were profound changes in gene expression in the atrophied introitus of post-menopausal subjects compared to the tissues of healthy premenopausal women, with several thousand differentially expressed genes (>5500 probe sets corrected for false discover at q<0.05). In contrast, there were far fewer significant gene expression changes in the labia majora of subjects with vaginal atrophy, consistent with the less severe changes in epithelial histology. Probe sets selected for hierarchical clustering were filtered for p<0.01 in either the Post-M to Pre-M or the Post-M to Post-M+HT comparisons (i.e., atrophied to non-atrophied). Additional filtering was done to eliminate probe sets with low signal. This yielded a total of 7488 probe sets for the introitus. The patterns of differential gene expression for the Post-M to Pre-M and Post-M to Post-M+HT introitus comparisons were remarkably similar. There was approximately 99% concordance between the directional patterns of gene expression in the Post-M comparisons to the Pre-M and Post-M+HT groups (up- and down-regulation). These results are believed consistent with the fact that the women on HT did not have signs and symptoms of vaginal atrophy and presented with normal histology. However, many of the post-menopausal changes in introital gene expression were possibly weakly evident in the group on HT, since the pattern of differential gene expression in Post-M+HT to Pre-M groups showed similarity to the Post-M to Pre-M comparison. In that case there was 82% directional concordance of the $\log_2$ fold changes for these two comparisons.

A similar pattern was seen in the labia majora for the Post-M comparisons to the Pre-M and Post-M+HT groups, but only 1169 probe sets met the statistical filtering criteria. The magnitude of differential gene expression in the various comparisons was generally smaller in the labia majora. For the labia majora there was >95% directional concordance in differential gene expression patterns for the Post-M comparisons to the Pre-M and Post-M+HT groups. Unlike the introitus, the Post-M+HT to Pre-M and Post-M to Pre-M comparisons were not very similar. The overall analyses for both the introitus and labia majora are believed to show that, compared to post-menopausal subjects with vaginal atrophy, the subjects on HT (and without vaginal atrophy) had global patterns of differential gene expression closely resembling those of the younger premenopausal subjects, although there are quantitative differences in gene expression between the groups.

Enrichment analysis for Gene Ontology (GO) terms and other sources of gene annotation is a common approach to identify biological patterns in large sets of differentially expressed genes. There is a common thread among the top up-regulated processes related to response to wounding, angiogenesis, cell migration/locomotion, and immune regulation. Among the down-regulated biological processes was "epithelial cell differentiation", consistent with the thinning epithelium. The other down-regulated biological processes all relate to metabolism including fatty acid, steroid, carbohydrate and hormone metabolism. Another down-regulated process was "pyridine nucleotide metabolism" (p=5.99E-03). That term is associated with several down-regulated genes in the pathway for the synthesis of NAD+, a key coenzyme involved in intermediary metabolism. Diminished levels of NAD+ have been strongly linked to aging, and it has been suggested that NAD+ precursors may be useful interventions to reduce age-related pathologies (see, e.g., Verdin E., "NAD+ in aging, metabolism, and neurodegeneration.", Science, 2015; 350(6265):1208-13 and Kaeberlein M et al., "Healthy aging: The ultimate preventative medicine.", Science, 2015; 350 (6265):1191-3). These results suggest that the skin anti-aging ingredient and NAD+ precursor, niacinamide, may have beneficial effects on atrophic vaginal tissue. A separate enrichment analysis using labia major data, which had far fewer significant genes, gave more limited results. However, for the Post-M to Pre-M labia majora group comparison the most significantly enriched terms were "immune response" (up-regulated, p=8.95E-05) and "collagen metabolic process" (down-regulated, p=2.19E-04), indicating some similarities in the aging of genital skin (labia majora) and mucosa (introitus). Additionally, there are several similarities between the processes altered during introital aging and those reported during skin aging including changes in epithelial differentiation and immune/inflammatory changes (see, e.g., McGrath J A et al., "Skin differences based on age and chronicity of ultraviolet exposure: results from a gene expression profiling study", Br J Dermatol. 2012; 166 Suppl 2:9-15; and Robinson M K et al., "Genomic-driven insights into changes in aging skin", J Drugs Dermatol. 2009; 8 (7 Suppl): s8-11).

A comparison was conducted between the results of this study and an earlier published study of vaginal atrophy (see, e.g., Cotreau M M, et al., et al., 2007, "A study of 17 beta-estradiol-regulated genes in the vagina of postmenopausal women with vaginal atrophy.", Maturitas, 58(4):366-376 and Jelinsky S A et al., 2008, "Molecular analysis of the vaginal response to estrogens in the ovariectomized rat and postmenopausal woman.", BMC Med Genomics, 1:27). In the earlier investigation, vaginal gene expression changes were studied in menopausal women between baseline and after 12 weeks systemic ET treatment with estradiol. The ET reversed atrophic changes in the vagina as indicated by reduced pH and increased VMI. Of the probe sets meeting the statistical filtering for the cross-study comparison, there were 734 from the HG-U219 GeneChip (current study) that mapped to 654 on the HG-U133 Plus 2.0 model (prior vaginal study), and these represent transcripts of 589 genes. The patterns of differential gene expression in atrophied versus non-atrophied tissues were remarkably similar for the introitus and vagina. Of the 589 genes only 2 showed directionally different patterns in the vagina and in introitus. This appears to demonstrate a remarkable similarity of two independent gene expression studies done in different laboratories and that there are many common changes in gene expression associated with atrophy in the introitus and the lower third of the vagina.

In summary, post-menopausal atrophy of the vaginal introitus and to a lesser extent the labia majora were associated with marked changes in epithelial histology and patterns of gene expression. The gene expression changes were consistent with epithelial thinning, remodeling of the dermal matrix, low level chronic inflammation and decreases in metabolic processes. It is presently believed that this study supports the potential utility of treatments for the vaginal introitus and, optionally, external vaginal tissues. Without intending to be bound by any theory, it is also presently believed that treatment of the vaginal introitus and, optionally, external vaginal tissues with non-hormonal vaginal care compositions (e.g., containing an anti-aging skin care agent) may provide beneficial results. While the applicators, kits and methods described herein are desirably used with non-hormonal vaginal care compositions, the disclosure is not so limited and compositions comprising an estrogen agent and/or a progesterone agent may also be employed.

B. Kits for use in Treating the Vaginal Introitus and, Optionally, External Vaginal Tissues Referring now to FIG. 1, an example applicator 100 in accordance with one non-limiting embodiment is depicted. The applicator may be combined with a vaginal care composition in a kit 110. The kit may comprise a single applicator that is reusable, or a plurality of applicators may be provided. As shown in FIG. 1, the kit 110 may further include a dispenser 104 or receptacle (not shown), in which the vaginal care composition is stored. The dispenser or receptacle is separate from the applicator 100. The kit 110 may further include a pouch 106, a cap, or a case, in which the applicator 100 and/or dispenser 104 may be stored before and after use. The applicator 100, dispenser 104 containing the vaginal care composition and the pouch 106 may be packaged together and sold as a packaged unit or sold separately.

As described in more detail below, the applicator 100 comprises an elongate body having a proximal end 114 and an insertion portion 116. In some examples, the vaginal care composition is applied to the insertion portion 116 to be administered to the vaginal introitus and/or one or more of the vulva, vestibule, labia majora, labia minora, and/or external urogenital tract to treat vaginal dryness and/or symptoms associated with vaginal atrophy.

i. Applicators a. Dimensions and Shapes

Figure 2:
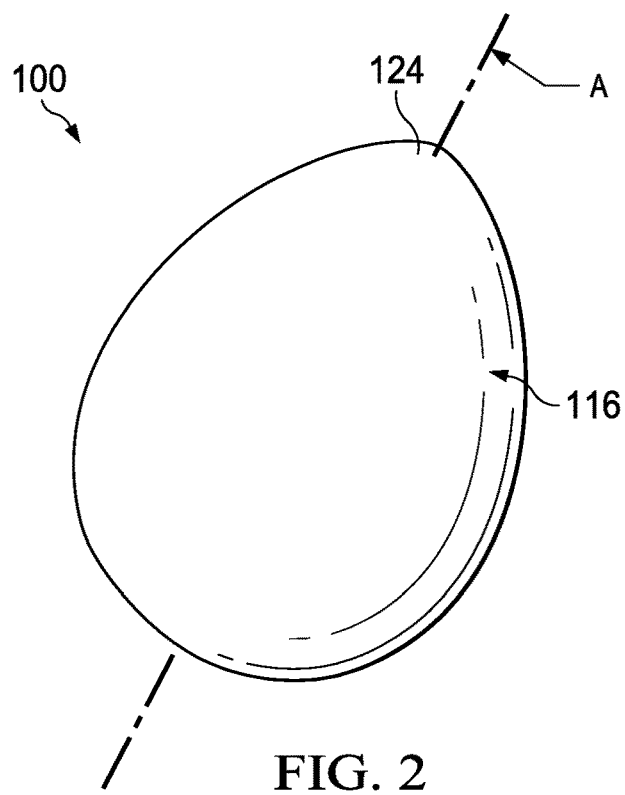
FIG. 2 is a perspective top view of the hand-held applicator of FIG. 1.
Figure 3:
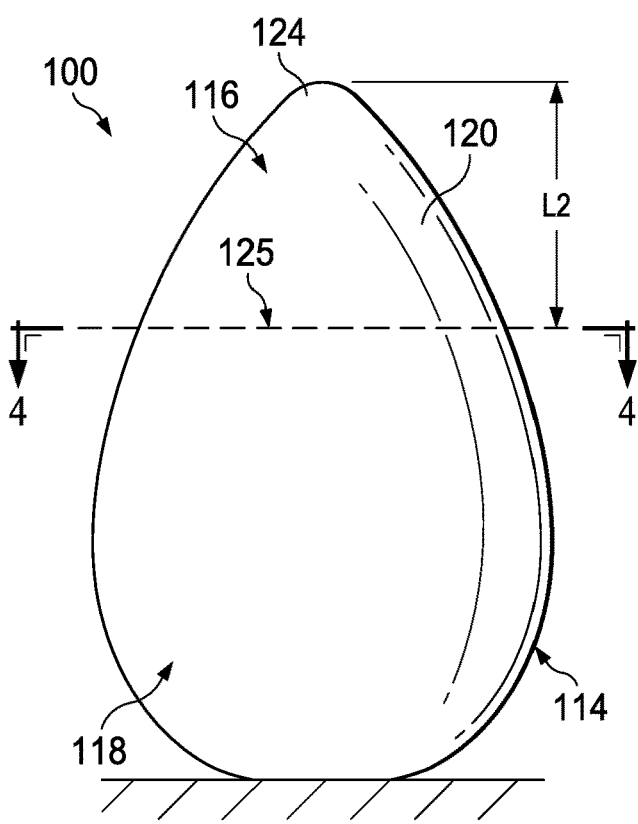
FIG. 3 is a front view of the hand-held applicator of FIG. 1 resting upright on a surface.
Figure 4:
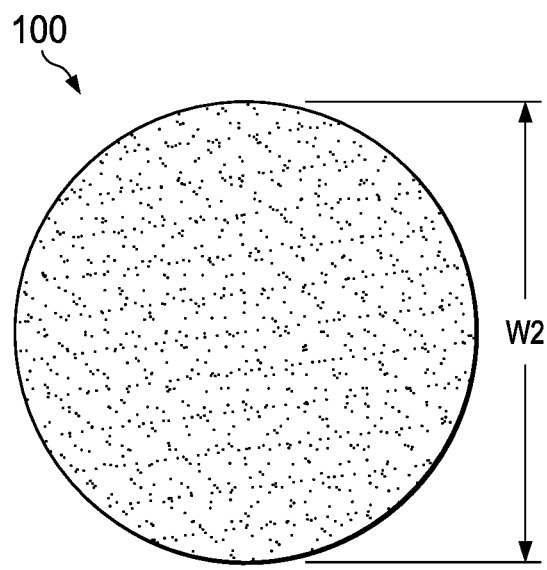
FIG. 4 is a cross-sectional view of the applicator of FIG. 3, taken along line 4-4 thereof.
Figure 5A:
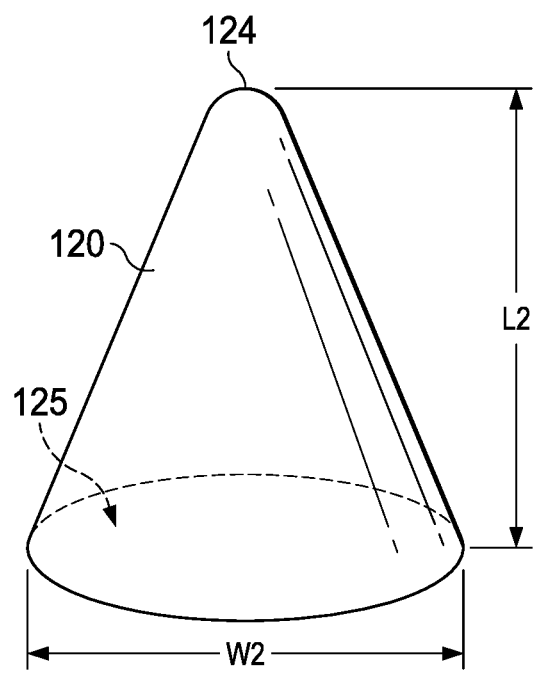
FIGS. 5A to 5G are perspective views of some non-limiting outer shapes that are suitable for use as cone-shaped insertion portions of an applicator.
Figure 5B:
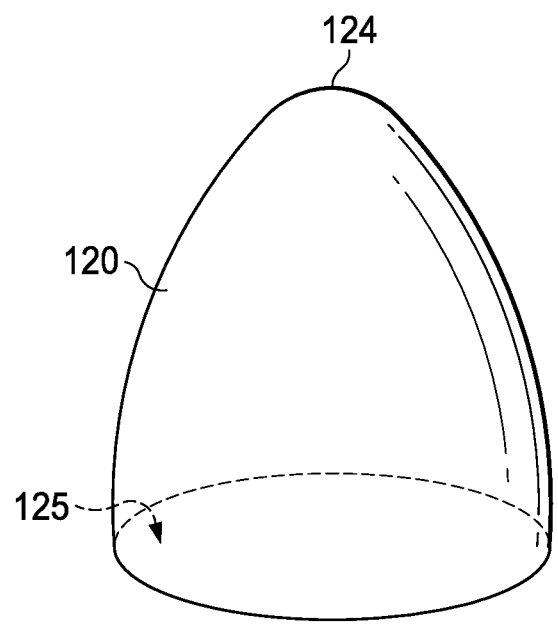
Figure 5C:
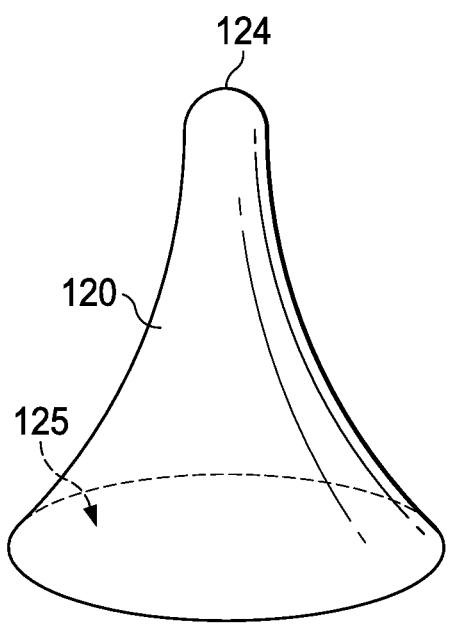
Figure 5D:
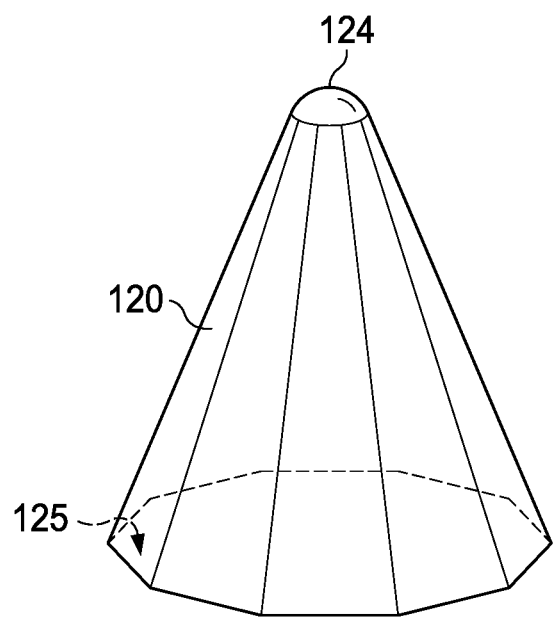
Figure 5E:
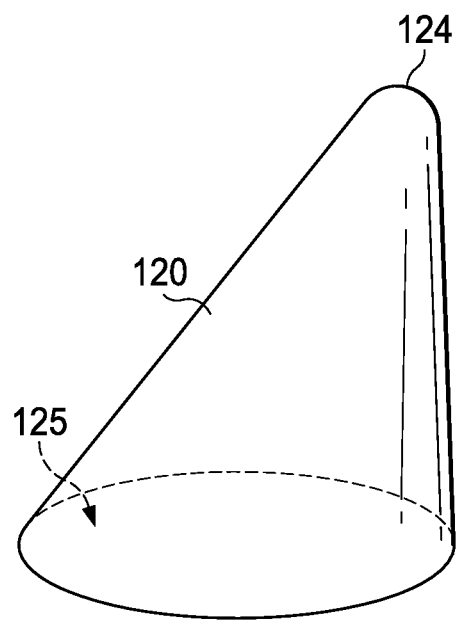
Figure 5F:
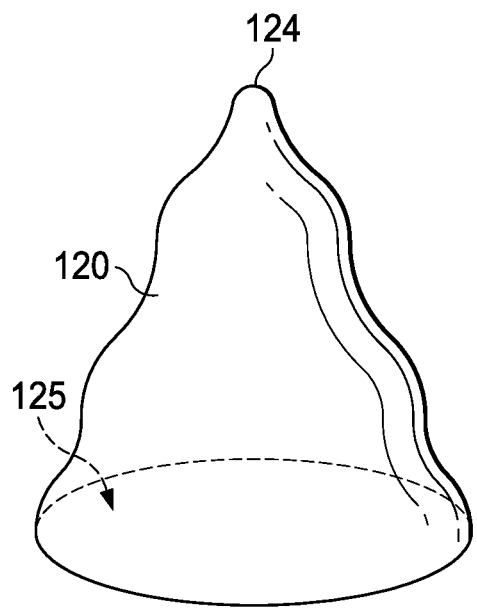
Figure 5G:
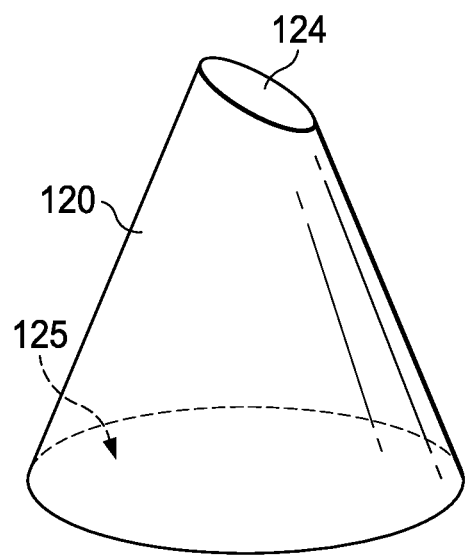

Referring now to FIGS. 2-4, one non-limiting example of an applicator 100 is depicted for applying a spreadable vaginal care composition to the vaginal introitus and/or one or more of the vulva, vestibule, labia majora, labia minora, and/or external urogenital tract while limiting or preventing the vaginal care composition from contacting the user's fingers during use. The applicator 100 comprises a body having a proximal end 114 and a tapered insertion portion 116 opposite the proximal end 114. The insertion portion 116 may be shaped and sized to accommodate the anatomical geometry of the vaginal introitus and for applying the vaginal care composition thereto. A vaginal care composition may be applied to the insertion portion 116 to be administered to the desired vaginal tissue.

Figure 9A:
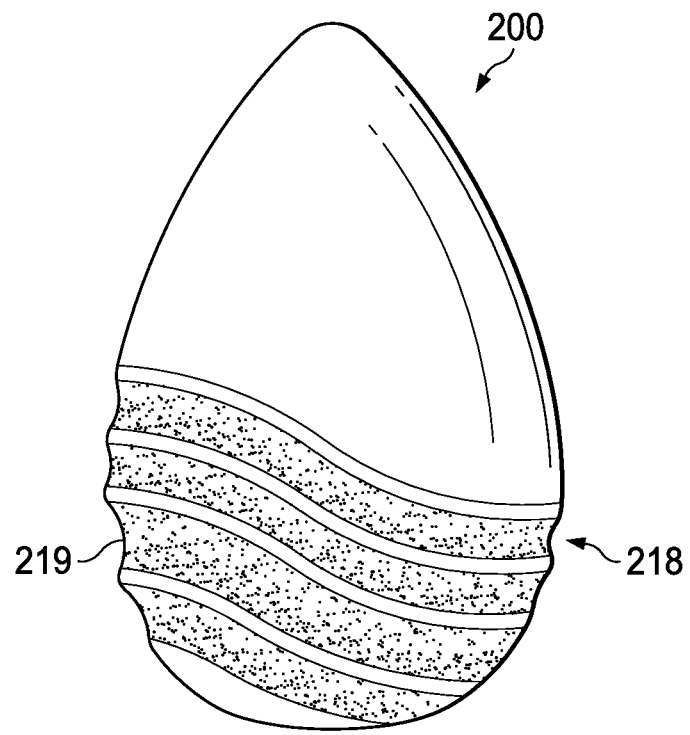
FIGS. 9A and 9B are front and rear views (the rear view being a mirror image of the front view) of a second example of an applicator, illustrating a grippable portion comprising a texture in the form of a plurality of grooves.
Figure 9B:
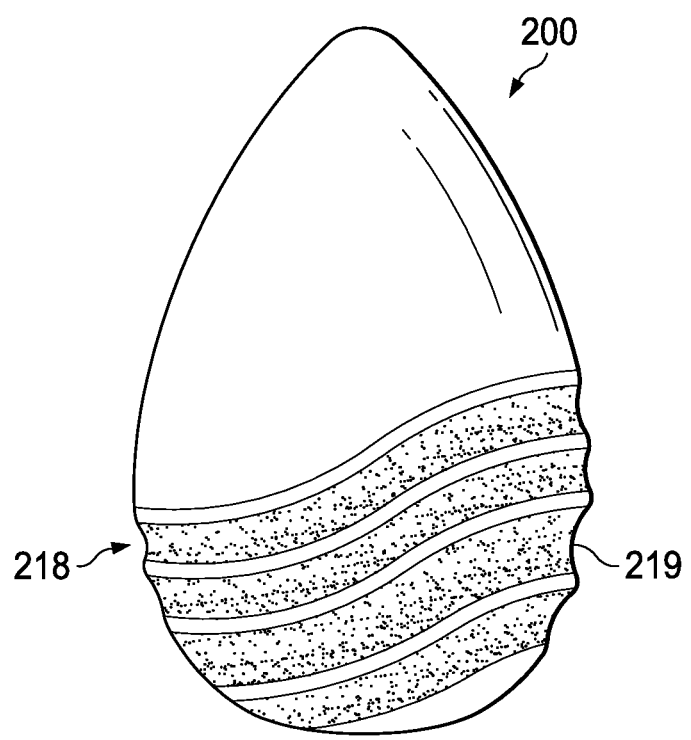

The insertion portion 116 comprises a tip 124. In some embodiments, the insertion portion 116 terminates at a longitudinal distance L2 from the tip 124, where the point of termination is referred to herein as a base 125 of the insertion portion 116. While the insertion portion may be described herein as terminating at the base for purposes of discussion, the base is not necessarily a distinct physical structure (although in some examples it may be) but rather a location along a longitudinal axis A defined by the length L2. In some examples, the insertion portion 116 may have a generally circular cross-section (shown by way of example in FIG. 4) at the base 125, although other cross-sectional shapes at the base (e.g., ovoidal, elliptical, hexagonal) are possible. The insertion portion 116 is preferably rotationally symmetrical about the longitudinal axis A, as this symmetry may facilitate easier usage and application of a vaginal care composition by a female user. In some embodiments, the insertion portion 116 has an overall shape that looks the same after an angular rotation thru a partial turn of 45°, 90°, 135°, 180°, 225°, 270° or 315° about its longitudinal axis. For example, the body of applicator 200 shown in FIGS. 9A and 9B is considered rotationally symmetrical thru 45°, 90°, 135°, 180°, 225°, 270°, 315° and 360° about the longitudinal axis of the applicator 200.

In some embodiments, the insertion portion is cone-shaped. Some non-limiting cone-shaped geometries are shown in FIGS. 5A to 5G, such as the right circular cone shown in FIGS. 5A, 5B and 5C the multi-faceted cone shown in FIG. 5D, the oblique cone shown in FIG. 5E, and the contoured cone shown in FIG. 5F. In some examples, a side profile of a lateral surface 120 of the cone shaped insertion portion may be at least partially convex (e.g., FIG. 5B), at least partially concave (e.g., FIG. 5C) or at least partially straight (e.g., FIG. 5A). The tip 124 of the insertion portion 116 may have any shape, including but not limited to rounded, concave, convex, flat, indented, angled or pointed. While the insertion portion may be provided in a variety of shapes, in some examples, the insertion portion has a continual taper, has a rounded tip, a substantially circular cross section at the base and a side or lateral surface that is slightly convex from the base to the rounded tip. One non-limiting example of such a cone-shaped insertion portion is shown in FIG. 3 in the context of applicator 100. The lateral, outer surface (e.g., 120 in FIG. 3) of the insertion portion 116 may be smooth (which also includes a surface comprising a micro-texture which may be provided, for example, by sand blasting injection molds for the body) so as to avoid irritation of the vaginal tissues during manipulation of the applicator to administer the vaginal care composition to the vaginal tissues of interest. Preferably, the micro-texture, while visible to a user, is not felt by a female user in use when the insertion portion is inserted into the vaginal introitus or rubbed against the external vaginal tissues of interest. In addition, a micro-texture can reduce soiling and/or tackiness of the insertion portion. The micro-texture may cover 50%, 60%, 70%, 80%, 90% or 100% of the insertion portion.

Figure 6:
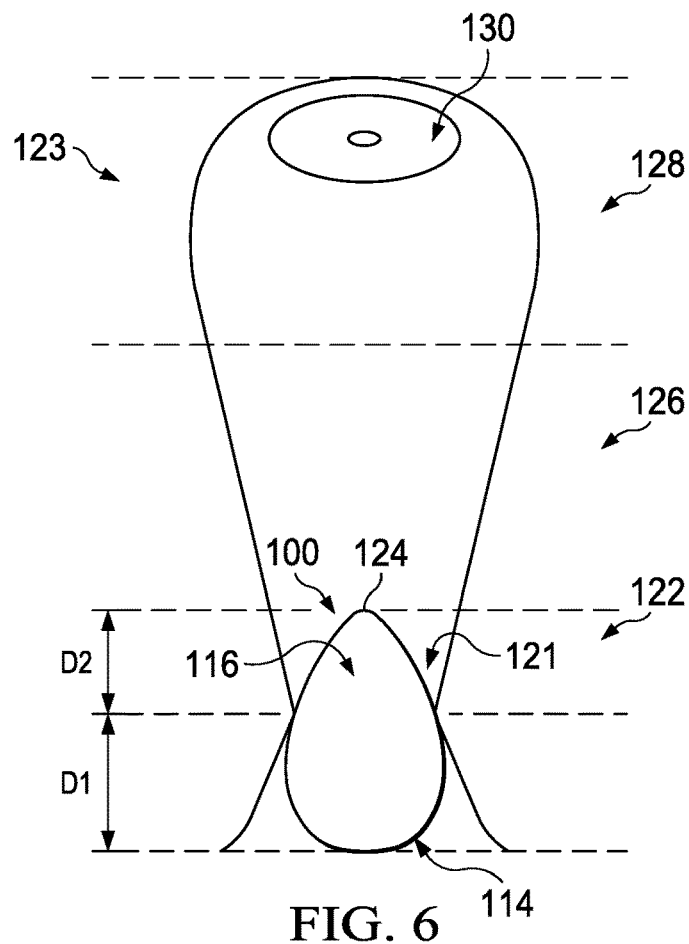
FIG. 6 is a schematic view, depicting the applicator of FIG. 2 in use and in contact with the vaginal introitus.

The dimensions and structural attributes of the insertion portion 116 may facilitate its use within the vaginal areas described above. While there may be considerable variability in vaginal shape, axis, and dimension from woman to woman, the dimensions and structural attributes of the insertion portion may be designed to accommodate the vaginal introitus, taking into consideration a wide range of anatomical measurements while also self-limiting the insertion depth of the applicator. Since the applicators may be used by women suffering from vaginal atrophy, the size and shape should also accommodate the anatomical changes that occur with vaginal atrophy. In a study by Luo et al. entitled, "Quantitative analyses of variability in normal vaginal shape and dimension on MR images" ("Luo et al."), magnetic resonance imaging (MRI) was used to take a series of measurements in order to quantify variability in vaginal dimensions for a group of women age 28 to 70. Luo et al. recognized that the vagina has three regions: a lower region (distal half of an anterior vaginal wall (AVW)), a middle region (proximal half of the AVW), and an upper region (cervical portion axis). Among its measurements, Luo et al. also assessed vaginal widths along a vaginal length. Luo et al. notes that the vaginal width is generally at its largest in an upper region of the vagina but generally decreases toward a lower region, such that the width is at its narrowest at the vaginal introitus. Lou et al. noted that the vaginal threshold (introitus) had a minimum dimension of 9 mm, maximum of 31 mm and mean of 17 mm, with a standard deviation of 5 mm, which may represent a dimensional range for peri- and post-menopausal woman. The schematic view depicted in FIG. 6 illustrates a narrowing vaginal width along a vaginal length to the vaginal introitus 121, which is shown to be in contact with the applicator 100. The insertion portion 116 of the applicator 100 is shown in FIG. 6 to extend a minimal distance thru the vaginal introitus.

Figure 7:
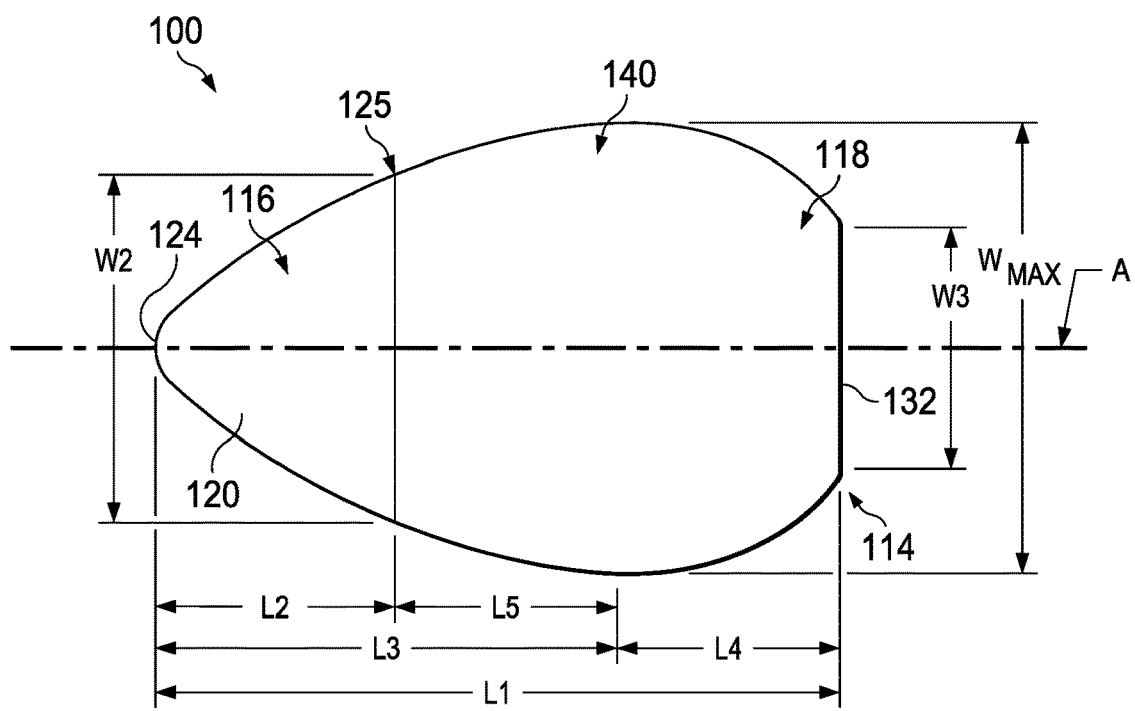
FIG. 7 is a side view of the applicator of FIG. 3, illustrating various dimensions.

Referring to FIG. 7, the insertion portion 116 may have a length L2 and a width W2, wherein the length L2 is intended to correspond to the desired depth of insertion of the insertion portion 116 into the vaginal introitus 121 during use and the width W2 is intended to correspond to the inner dimensional width of the vaginal introitus opening 121, taking into account the various dimensions of the vaginal introitus 121 across a population of users, including women suffering from vaginal atrophy. With respect to an applicator 100, the length L2 of the insertion portion 116 refers to the longitudinal distance extending from the tip 124 of the insertion portion 116 toward the proximal end 114 of the applicator 100, shown by way of example in FIG. 7. The terminal end of the length L2 opposite the tip 124 defines the location of the base 125 of the insertion portion 116. Stated differently, the base 125 of the insertion portion 116 may be located a distance L2 from the tip 124 of the insertion portion 116. In some examples, the length L2 of the insertion portion 116, taken along the longitudinal axis A, may be from about 10 mm to about 40 mm, or from about 10 mm to about 35 mm, or from about 10 mm to about 30 mm, or from about 10 mm to about 25, from about 10 mm to about 20 mm, where such lengths may correspond to an estimated distance from the vaginal introitus 121 to a proximal portion of the lower region 122 (e.g., D2 of FIG. 7). The width W2 of the insertion portion 116 is the width taken at the location of the base 125 (which is defined by the terminal end of the length L2 as previously described). In some examples, the tip 124 of the insertion portion 116 has a width that is less than a width W3 of the proximal end 114, as shown by way of example in FIG. 7.

Maximum and minimum values for the width of the vaginal introitus are believed to be about 9 mm and about 31 mm, respectfully. In some examples, a radial width W2 of the insertion portion 116 at the base 125, which is shown in FIG. 7, can be from about 10 mm to about 40 mm; from about 15 mm to about 35 mm, from about 20 mm to about 30 mm; or any value from about 10 mm to about 40 mm or any range formed by any of the preceding values. When a length L2 is provided herein as a range (e.g., between X mm and Y mm) together with a width W2 provided as a range (e.g., between Amm and Bmm), then this combination is satisfied if either, at the length X, the width is between about A and B or, at the length Y, the width is between A and B. In some examples, the width W2 of the base 125 may also be the maximum width of the insertion portion 116 in order to limit the distance the applicator 100 is inserted into the vaginal introitus using gentle hand pressure (and without experiencing discomfort) and/or to signal to a user that the appropriate insertion depth has been achieved during use.

In some examples, it may be desirable for the applicator to be dimensioned to prevent over-insertion of the applicator into the vaginal canal. For example, the insertion portion 116 or another portion of the body may further exhibit dimensions that provide a self-limiting feature with respect to insertion beyond the lower region 122 of the vagina 123, such that in some examples, contact between the insertion portion 116 and either of a middle region 126 or an upper region 128, including the cervix 130, is avoided, as illustrated in FIG. 6. For example, and as best shown in FIG. 7, a maximum width $W_{max}$ of the body may be greater than the width W2 of the base 125 of the insertion portion 116, wherein the maximum width $W_{max}$ of body may be disposed along the longitudinal axis A between the proximal portion 114 and the base 125 of the insertion portion 116. In some examples, the maximum width $W_{max}$ can be from about 20 mm to about 80 mm, or from about 20 mm to about 60 mm, or from about 25 mm to about 70 mm, or from about 25 mm to about 55 mm, or from about 30 mm to about 50 mm or any value from about 20 mm to about 80 mm, or any range formed by any of the preceding values. The longitudinal distance L3 from the tip 124 of the insertion portion 116 to the location of the maximum width $W_{max}$ may be, in some examples, from about 35 mm to about 90 mm, or from about 35 mm to about 60 mm, or from about 40 mm to about 50 mm or any value from about 35 mm to about 90 mm, or any range formed by any of the preceding values. The distance L3 preferably corresponds to a minimum of the combination of the estimated distances from the distal portion of the labia to the vaginal introitus (e.g., D1 of FIG. 6), which may be about 10 mm, and from the vaginal introitus to the proximal portion of the lower region (e.g., D2 of FIG. 6), which may be up to about 25 mm. In such examples where the insertion portion 116 fails to exhibit dimensions that limit insertion beyond the vaginal introitus and lower region of the vagina, the portion of the body defining its maximum width $W_{max}$ may provide such a self-limiting feature (i.e., width) to prevent further insertion of the applicator through the vaginal introitus.

Figure 8:
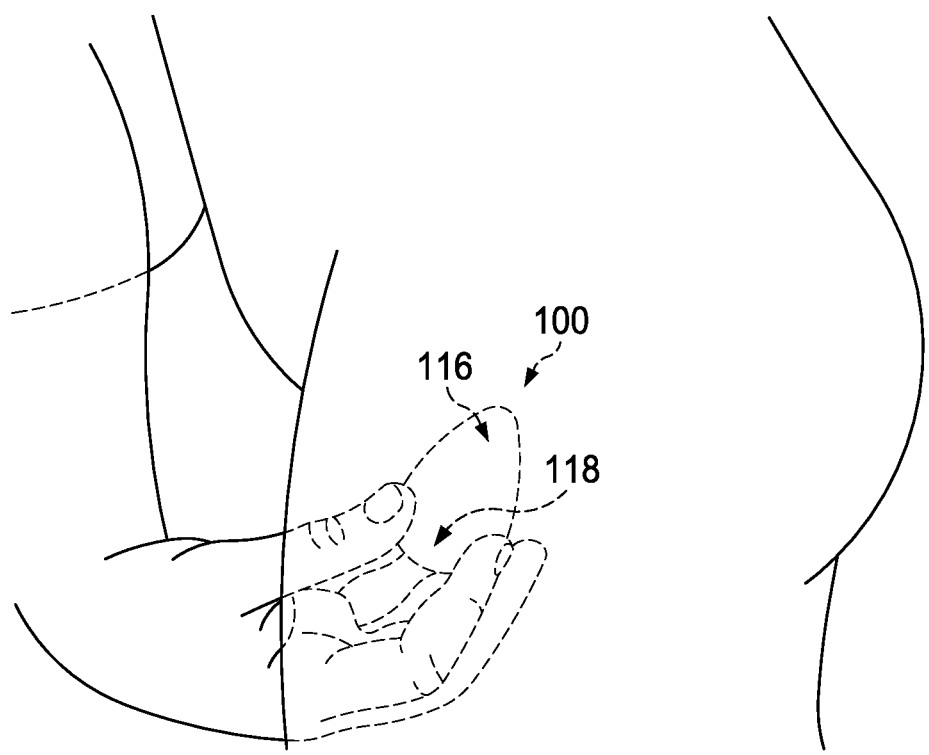
FIG. 8 is a schematic illustration of one use of the applicator of FIG. 2.

Referring again to FIG. 7, a grippable portion 118 may be provided adjacent the proximal end 114. In some examples, the grippable portion 118 may extend from the proximal end 114 to a terminal end of the length L4. The proximal end 114 has a width W3, which may be, in some examples, a width sufficient to allow the applicator 100 to remain standing in an upright position on a surface (e.g., a countertop), as shown, for example, in FIG. 3, without falling over. In some examples, the width W3 is about 80 mm or less, or from about 15 mm to about 60 mm or from about 20 mm to about 40 mm. A proximal end having a width within these ranges may be believed to be desired as these values provide a starting size for the grippable portion that is comfortable for gripping with at least 2 fingertips. In some instances, the grippable portion may be grasped by 3, 4 or 5 fingertips. Thus, while holding the applicator 100 at the grippable portion 118, a female user may apply the vaginal care composition to a lateral surface 120 of the insertion portion 116 and administer the vaginal care composition to desired vaginal tissue by contacting at least the vaginal introitus and, optionally, one or more of the vulva, vestibule, labia majora, labia minora, and/or external urogenital tract with the insertion portion 116 such that at least a portion of the vaginal care composition thereon is transferred to the vaginal tissue. One non-limiting illustration of the manner of grasping a grippable portion 118 and inserting the applicator 100 into the vaginal introitus is shown in FIG. 8, wherein the applicator is illustrated as grasped by 5 fingertips. In some instances, the applicator is grasped by only the fingertips (versus the palm of the hand or lower finger knuckles) to permit easy manipulation of the applicator and administration of the vaginal care composition to the vaginal tissues of interest.

1. In some examples, the grippable portion 118 may extend along a longitudinal length L4 (FIG. 7) from the proximal end 114. As described herein, the grippable portion 118 preferably remains external to the labia during use, which assists with keeping the fingers of the female user clean during use of the applicator. In some examples, the longitudinal distance L4 from the proximal end 114 may be from about 5 mm to about 65 mm, or from about 10 mm to about 65 mm, or from about 10 mm to about 50 mm, or from about 20 mm to about 40 mm, or any value from about 10 mm to about 65 mm, or any range formed by any of the preceding values.

In some examples, the grippable portion may be defined by a texture or visual indicator.

Some non-limiting examples of various grippable portion configurations having a texture are shown in FIGS. 9 to 16. The texture may comprise a plurality of protrusions, a plurality of recesses and combinations thereof. In some embodiments, the texture may be provided as a plurality of ridges, a plurality of grooves and combinations of the foregoing. While a texture is shown in these FIGS. 9 to 16, the grippable portion may alternatively or in addition thereto be provided with a surface finish (e.g., micro-texture) or surface treatment (e.g., dip coating, spray coating, printing) that enhances the grippability of the grippable portion. The texture, surface finish or surface treatment may partially or wholly encircle the body. The texture may have a maximum height or maximum depth from about 0.1 mm to about 5 mm, or from about 0.1 mm to about 4 mm, or from about 0.25 mm to about 3 mm, or from about 1 mm to about 2 mm or any value from about 0.1 mm to about 5 mm or any range formed by any of the preceding values. The texture may be provided as a repeating, preferably regularly repeating, pattern, although random or irregular patterns may also be provided. Further, the texture may be provide in the shape of objects, some non-limiting examples being leaves, flowers, stars and geometric shapes (e.g., FIGS. 13, 14 and 15). The texture may also be provided as a repeating, closed geometric shape, some non-limiting examples being circles, diamonds, triangles, rectangles and combinations thereof (see, e.g., FIGS. 16 and 17).

Figure 10:
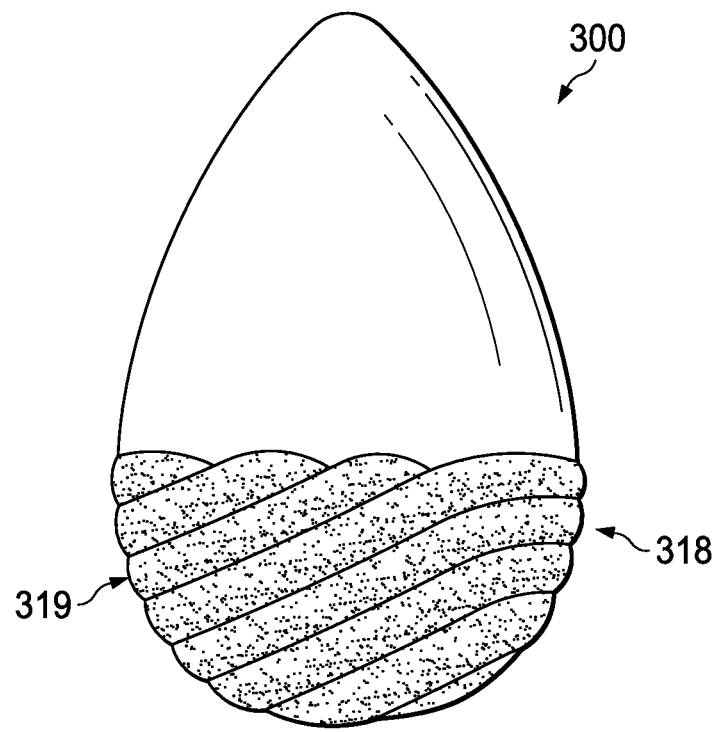
FIG. 10 is a front view of a third example of an applicator, illustrating a grippable portion comprising a texture in the form of a plurality of ridges (the rear view, not shown, being a mirror image of the front view)
Figure 11:
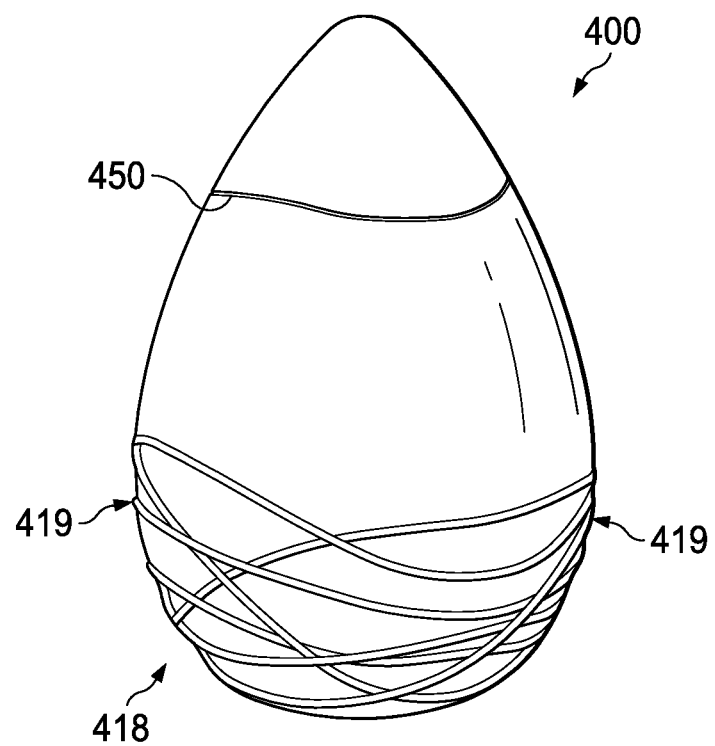
FIG. 11 is a front view of a third example of an applicator, illustrating a grippable portion comprising a texture in the form of a plurality of ridges.
Figure 12:
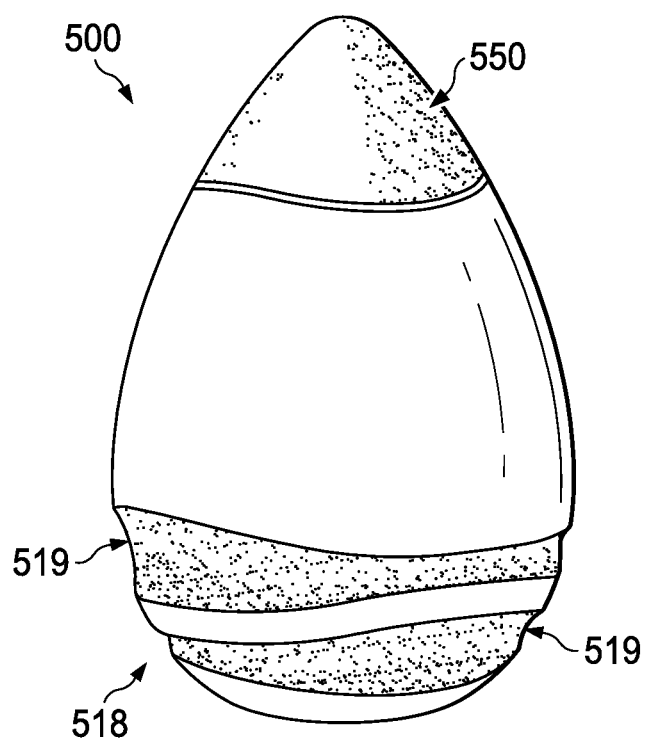
FIG. 12 is a front view of a fourth example of an applicator, illustrating a grippable portion comprising a texture in the form of a plurality of grooves (the rear view, not shown, being the same as the front view)
Figure 13:
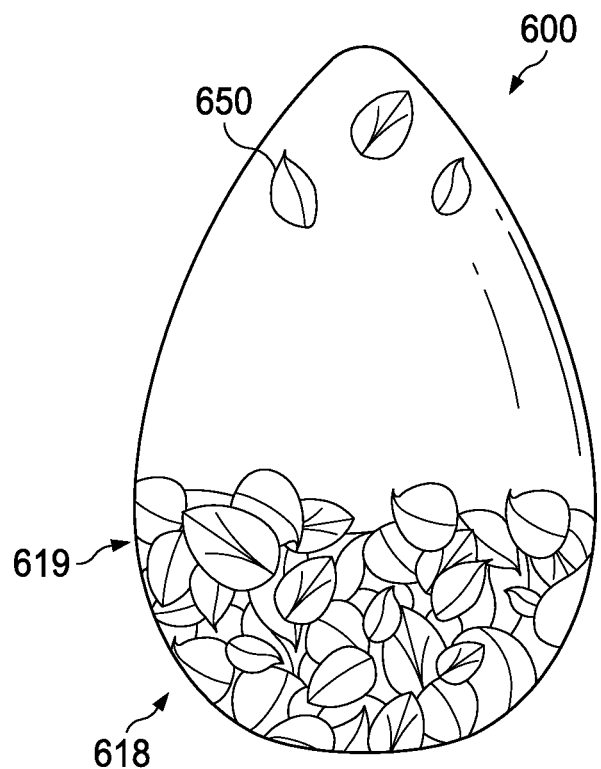
FIG. 13 is a front view of a fifth example of an applicator, illustrating a grippable portion comprising a texture in the form of a plurality of leaves.
Figure 14:
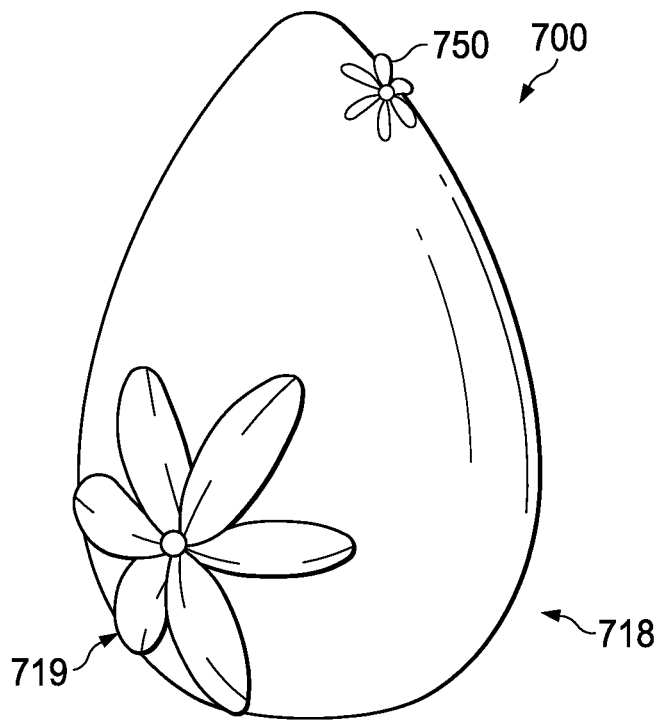
FIG. 14 is a front view of a sixth example of an applicator, illustrating a grippable portion comprising a texture in the form of a flower.
Figure 15:
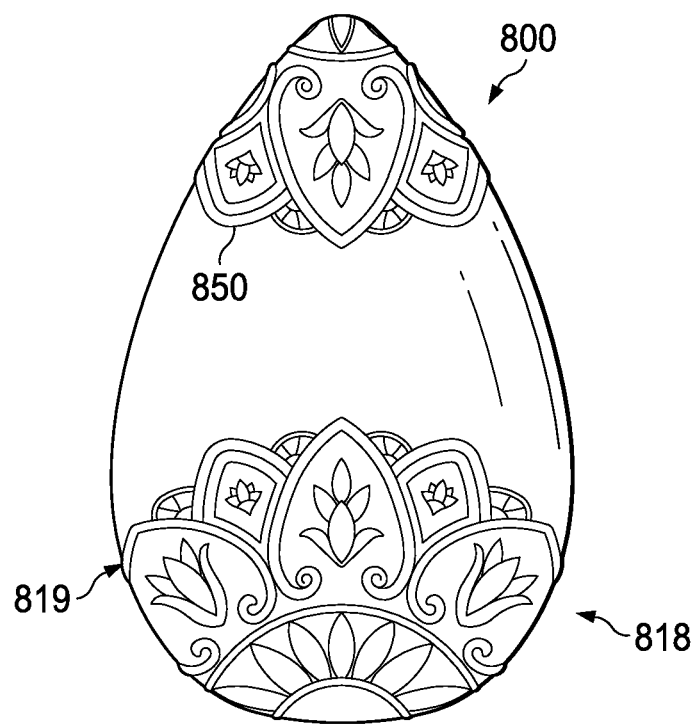
FIG. 15 is a front view of a seventh example of an applicator, illustrating a grippable portion comprising a texture in the form of a geometric pattern (the rear view, not shown, being the same as the front view)
Figure 16:
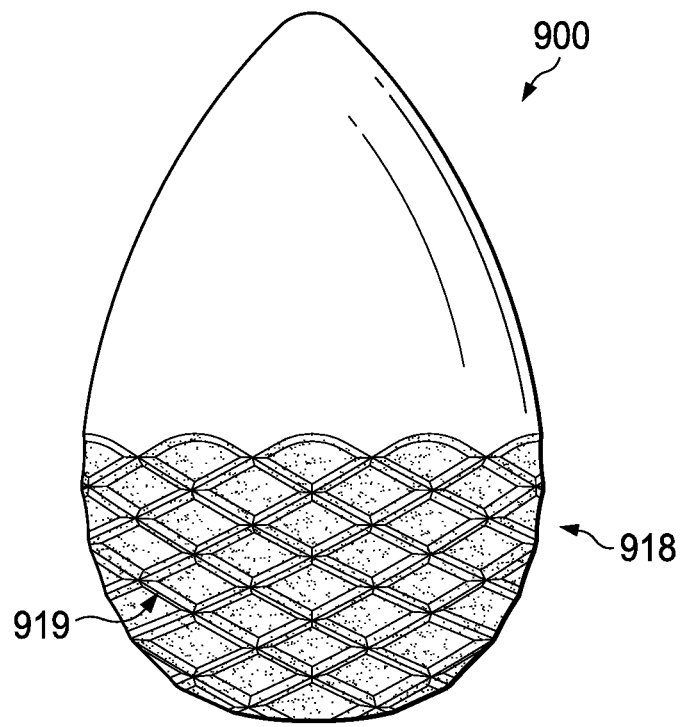
FIG. 16 is a front view of an eighth example of an applicator, illustrating a grippable portion comprising a texture in the form of a geometric pattern (the rear view, not shown, being the same as the front view)
Figure 17:
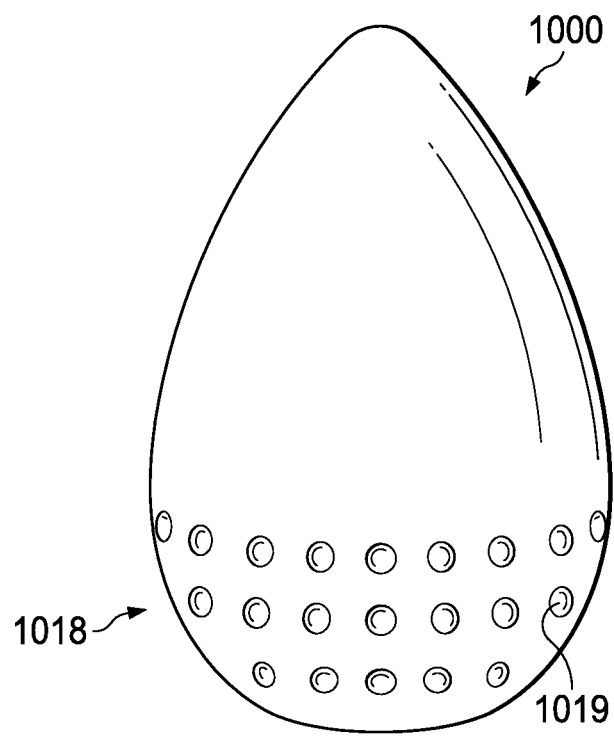
FIG. 17 is a front view of a ninth example of an applicator, illustrating a grippable portion comprising a texture in the form of pattern of dimples (the rear view, not shown, being the same as the front view)

One non-limiting example of a texture is depicted in the applicator 200 of FIGS. 9A and 9B, where the grippable portion 218 comprises a plurality of grooves 219 arranged in a repeating pattern. While FIG. 9 illustrates a texture that extends about the entire circumference or lower outer surface of the applicator, the disclosure is not so limited. In other embodiments, the texture or surface finish/surface treatment may extend about only a portion of the circumference or lower outer surface of the applicator. In some embodiments, the texture may extend from the proximal end to the maximum width $W_{max}$. In another non-limiting example, FIG. 10 illustrates an applicator 300 having a grippable portion 318 comprising a plurality of protruding ridges 319 arranged in a repeating pattern. FIG. 11 illustrates an applicator 400 comprising a plurality of thinner ridges 419 arranged in an irregular pattern. FIG. 12 illustrates an applicator 500 having a plurality of grooves 519. FIG. 13 illustrates an applicator 600 having a texture in the form of raised leaves 619, and FIG. 14 illustrates an applicator 700 having a texture in the form of a raised flower 719. FIG. 15 illustrates an applicator 800 having a raised geometric pattern 819 which includes in the center a depiction of a flower. FIG. 16 illustrates an applicator 900 having a texture provided as a plurality of recessed diamonds 919 arranged in a repeating pattern. FIG. 17 illustrates an applicator 1000 having a texture in the shape of a plurality recessed dimples 1019 arranged in a repeating pattern. It will be appreciated that any of the textures described above as recessed may alternatively be provided as a protrusion and vice versa.

In some examples, the texture, surface finish or surface treatment may extend about 10 mm or more from the proximal end of the applicator. These features may identify the grippable portion to a user and therefore also function as a visible indicator of the location of the grippable portion. In some examples where grooves or ridges are provided, a groove or ridge width may be greater than the groove or ridge height to minimize gathering or collection of the vaginal care composition and/or provide for easy rinsing and cleaning of the applicator after use.

Figure 18:
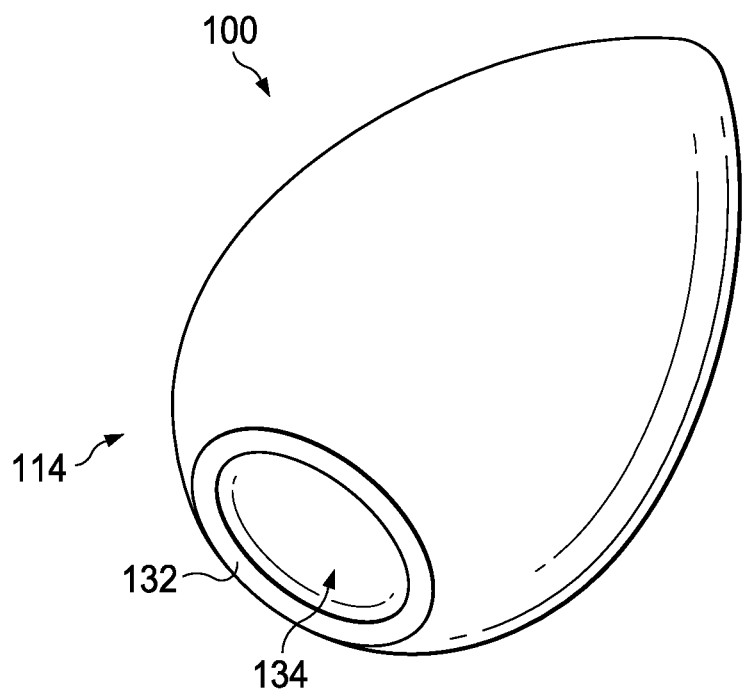
FIG. 18 is a perspective bottom view of the applicator of FIG. 3, illustrating a proximal end comprising a substantially flat portion and an indentation.

In some examples, the proximal end, or a portion thereof, may be substantially flat. As shown for example in FIGS. 3 and 18, proximal end 114 of applicator 100 includes a flat portion or bottom 132 which can allow a user to stand the applicator 100 in an upright position on a surface before and after use, such that it can be oriented in a way to minimize or prevent contact between a resting surface and the insertion portion of the applicator 100. The proximal end 114 of the applicator 100 may comprise an indentation 134 which is partially or wholly encircled by the flat portion 132, which can allow a user to further minimize or prevent contact between a resting surface and the applicator 100. While the proximal end 114 of the applicator 100 is shown in FIG. 18, for example, as having a substantially flat or planar portion, the disclosure is not so limited and the proximal end may be provided in other shapes, such as, for example, rounded, partially rounded or any other suitable shape. Likewise, while the grippable portions illustrated, for example in FIG. 7, is shown as tapering from the maximum width $W_{max}$ to the proximal end 114, the shape of outer surface of the grippable portion may be provided in other shapes (e.g., non-tapered).

In some examples, the applicator may further comprise an intermediate portion disposed between the insertion portion and the grippable portion. For example, and with reference to FIG. 7, the applicator 100 can include an intermediate portion 140. The intermediate portion has a length L5, which may be, in some examples, from about 25 mm to about 80 mm, or from about 25 mm to about 70 mm, or from about 30 mm to about 60 mm or any value from about 25 mm to about 80 mm or any range formed by any of the preceding values. The length L5 may provide a sufficient length to account for the distance D1 (FIG. 6) from the vaginal introitus 121 to the distal portion of the labia (e.g., about 10 mm) plus some additional distance (e.g., about 15 mm) to reduce the risk that the fingertips of the female user which grip the grippable portion 118 will contact the external vaginal tissues during use. In some examples, the maximum width $W_{max}$ of the applicator may be disposed within the intermediate portion 140. In some examples, the maximum width $W_{max}$ is located in the lower one half of the body (e.g., closer to the proximal end than the tip). In some examples, the maximum width $W_{max}$ of the applicator 100 may delineate a transition from the intermediate portion 140 to the grippable portion 118. In some examples, such as applicator 100, the body of the applicator continually tapers from the maximum width $W_{max}$ to the tip of the insertion portion (see, e.g., FIG. 3) and/or the lateral outer surface of the intermediate portion is smooth given it's possible this surface may contact external vaginal tissues during use and/or may be additionally used to apply the vaginal care composition to these external vaginal tissues.

Figure 19:
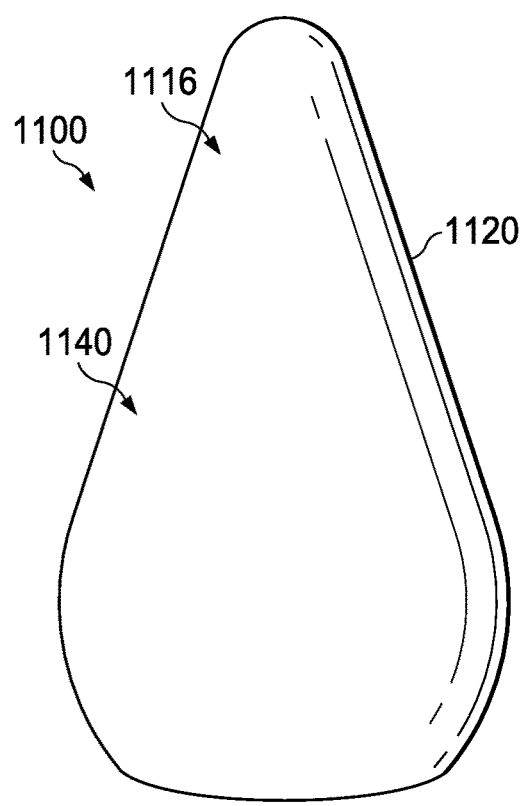
FIG. 19 is a front view of a ninth example of an applicator, illustrating a tear drop shaped profile (the rear view, not shown, being the same as the front view)
Figure 20:
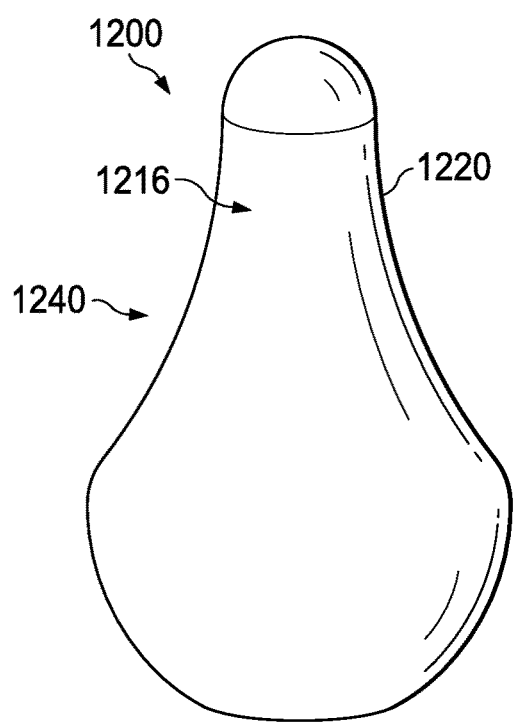
FIG. 20 is a front view of a tenth example of an applicator, illustrating a pear shaped profile (the rear view, not shown, being the same as the front view)

In some examples, the lateral, outer surface of the intermediate portion may be a simple continuation of the geometry of the insertion portion, for example as shown in FIG. 19 wherein the continual taper of the lateral surface 1120 of the insertion portion 1116 of applicator 1100 transitions seamlessly to and continues along the intermediate portion 1140, resulting in a tear dropped shaped profile. In contrast, with reference to FIG. 20, lateral surface 1220 of the insertion portion 1216 of applicator 1200 transitions to a new geometric shape (slightly concave) within the intermediate portion 1240, resulting in a generally pear-shaped profile.

Referring to FIG. 6, the overall length L1 of the applicator 100 may minimize or prevent contact between a female user's fingers and the vaginal areas described above while providing for an appropriate insertion depth slightly beyond the vaginal introitus. In some examples, the length L1 of the applicator may be from about 20 mm to about 90 mm, or from about 35 mm to about 85 mm, or from about 30 mm to about 80 mm, or from about 40 mm to about 70 mm, or from about 45 mm to about 65 mm or any value from about 20 mm to about 90 mm or any range formed by any of the preceding values. In some examples, a ratio of the length L1 of the applicator to the maximum width $W_{max}$ of the applir may be from about 1:2 to about 5:1, from about 1:1 to about 4:1 or any range formed by any of the preceding values. In some examples, a ratio of the length L3 to the length L4 may be from about 1:1 to about 9:1; in some examples, the ratio of the length L3 to the length L4 may be from about 1:1 to about 4:1; and in some examples, the ratio of the length L3 to the length L4 may be from about 1.5:1 to about 3:1. It is believed that the aforementioned lengths, widths and ratios may provide an applicator that balances an appropriate insertion depth, provides a grippable portion that may remain external to the vaginal tissues of interest, reduces the risk over-insertion (including "losing" the applicator within the vaginal canal during use), and facilitates appropriate spreading of the vaginal care composition about the vaginal tissues of interest, while taking into account anatomical variability between female users, including those experiencing vaginal atrophy.

While a variety of overall shapes may be provided for an applicator, the applicator 100 shown in FIG. 3 may be further described as substantially ovoidal, or egg-shaped in profile and rotationally symmetrical thru 360° of angular rotation about the longitudinal axis A thereof, although it is recognized that bodies of other applicators may be rotationally symmetrical thru less than 360° (e.g., 45°, 90°, 135°, 180°, 225°, 270°, 315° or 360°). It is believed this geometric shape is desirable for application of a spreadable vaginal care composition to the vaginal introitus and optionally the vulva, vestibule, labia majora, labia minora, and/or external urogenital tract. This shape may also be particularly useful in the case of women suffering from vaginal atrophy, given the variability in shape and size of this vaginal tissue between users as well as the sensitivity of these tissues. It is also believed that this shape can facilitate grasping and manipulating the applicator by a user to apply the vaginal care composition easily while in a variety of positions (e.g., seated, standing or laying down) and without viewing the tissues of interest during use.

The applicators may be devoid of moving parts, electrically powered elements (e.g., motors, lights, circuits, buzzers, speakers, etc.) and/or electrical power sources (e.g., batteries) to provide an applicator that is simple to manufacture and also easily immersed in or rinsed with water for cleaning. An applicator that is devoid or substantially free of batteries and/or electrically powered elements (e.g., motors, lights, etc.) is referred to as a non-electrical applicator. In some examples, at least 60%, 70%, 80%, 90%, 95% or 100% of the bulk volume is solid volume, preferably formed from a homogenous solid. Further, the body may be devoid or substantially free of chambers for storing or containing a flowable composition and/or passages, conduits, channels and/or openings or ports for delivering such a composition to an outer surface thereof (e.g., the insertion portion or its tip). Similarly, the body may be devoid of plungers and other structures that may be used to expel a vaginal care composition from the body of the applicator. In some examples, the body of the applicator is not phallic shaped so its appearance is more like a beauty care inspired device rather than a sexual or medicinal device, which, it is believed may be less intimidating and can inspire long term habit adoption by a female user.

b. Materials, Properties and Construction

The applicator and/or the materials used to form the applicator, may exhibit one or more properties suitable for applying a vaginal care composition to the vaginal introitus and, optionally, the vulva, vestibule, labia majora, labia minora, and/or external urogenital tract, some of which may be more delicate, sensitive, or fragile in women with vaginal atrophy. The applicator and/or the materials used to form the applicator may also be facilitate the grippability, re-usability and cleanliness of the applicator.

For example, the applicator, portions of the applicator (e.g., the insertion portion and/or the grippable portion) and/or materials used to form the applicator preferably exhibit tensile properties (e.g., peak compressive force) and/or durometer that provide sufficient rigidity for the insertion portion to be directed into the vaginal introitus with limited force (e.g., slight hand pressure) while still providing a consumer acceptable surface for administering the spreadable vaginal care composition to the vaginal tissues of interest (e.g., sufficiently compliant) as well as a compliant grippable portion.

It is believed certain applicator properties (e.g., Peak Force) provide a beneficial consumer experience. For example, a Peak Force (Tip) that is too high might create a perceived deterrent to regular use (e.g., might be perceived as uncomfortable or stretching tissues, etc.) while a Peak Force (Tip) that is too low may not easily spread the vaginal tissues or provide sufficient sensorial feedback regarding how far the applicator has been inserted or as to what tissues are in contact with the applicator tip. A Peak Force (Lateral Surface) that is too high may be less deformable and therefore less grippable while a Peak Force (Lateral Surface) that is too low may result in an applicator that is more difficult to manipulate and control using fingertips. In some examples, the applicator may exhibit a Peak Force (Tip) from about 0.1N to about 40N, from about 0.2N to about 10N, or from about 0.3N to about 5N. In some examples, the applicator may exhibit a Peak Force (Lateral Surface) from about 0.4N to about 90N, from about 0.7N to about 20N, or from about 0.9N to about 10N.

In some examples, the materials(s) used to form at least a portion of the applicator (preferably all of the body) can exhibit a hardness from about 20 Shore OO to about 60 Shore A, from about 60 Shore OO to about 40 Shore A, from about 5 Shore A to about 30 Shore A or any range formed by any of the preceding values. The durometer may be based upon the manufacturer's specifications for the material used to form the applicator, or, if not available, measured according to Deutsches Institut für Normung (DIN) 52505. Durometer, when available, may be a material property that is also useful for defining the deformability/grippability of the applicator, in place of Peak Force.

Portions of the applicator (e.g., the insertion portion, the grippable portion, and/or the intermediate portion) or the applicator overall may also have a low absorbency so that the applicator may be easily cleaned and remain sanitary due to little or no absorption of the vaginal care composition, cleaning fluids and/or bodily fluids by the applicator. In some examples, the applicator (or portions thereof) exhibits an absorbency less than 10% or from about 0.01% to about 2%, or from about 0.05% to about 1%.

In some examples, portions of the body, or the overall body, are formed from one or more of a thermoplastic elastomer, a natural rubber, a synthetic rubber (e.g., a silicone elastomer/silicone rubber), a polyester (e.g., a polyurethane, such as STERALLOY® 2021-5 available from Hapco, Inc.) and/or a thermoplastic olefin. In some examples, a portion of the body or the body overall is formed from a cross-linkable liquid silicone rubber that is subsequently cross-linked during the manufacturing process. The cross-linking can be accomplished in many ways as known in the art, one method being by the addition of a cross-linking agent (e.g., platinum) to the cross-linkable liquid silicone rubber during injection molding or casting of the body. The material used to form the body is preferably medical grade and preferably a medical grade cross-linkable silicone rubber which may have a Shore A hardness from about 5 to about 30. Some non-limiting examples of suitable materials from which to form the body of the applicator include Dow Corning® QP1-230; Dow Corning® QP1-240; Dow Corning® QP1-250; Dow Corning® QP1-260; Dow Corning® QP1-270; Dow Corning® QP1-20; SILPURAN® 6000/05, 6000/10, 6000/20, 6000/30; and ELASTOSIL® 3003/03, 3003/05, 3003/10, 3003/20, 3003/30 (available from Wacker). In some examples, the insertion portion and the grippable portion are formed from the same material or materials, while in other examples, the insertion portion and the grippable portion are formed from different materials. For example, an insertion portion may comprise a first material (e.g., a first elastomer) and a grippable portion may comprise a second material (e.g., a second elastomer) that is different from the first material. In some examples, however, the body of the applicator consists essentially of a single material (e.g., a cross-linked silicone rubber), although even in such examples it will be appreciated that the body may still comprise, for instance, impurities, pigments or other colorants, finishing aids, remnants of a cross-linking agent, etc. In some embodiments, the body may be integrally formed from or integrally comprise two or more materials, pieces or parts. For instance, two or more materials may be injection molded to form the body (e.g., one being a cross-linkable silicone rubber) or the body may be formed from a single material by injection molding and thereafter a coating of a second material is applied thereto (perhaps by over molding) or first and second portions, pieces or parts are formed (e.g., by injection molding) and the two portions are integrally connected either during the forming processes or thereafter (e.g., by mechanical fastening or chemical bonding). In some examples, the body, or a portion thereof, may be formed by injection molding or casting. When the body is formed by injection molding, the insertion portion may be devoid of part lines in order to provide a non-irritating surface. Stated another way, the part line may be located outside of the insertion portion. In some embodiments, the part line may be disposed circumferentially about the body at or near the maximum width $W_{max}$.

To further facilitate the ability of the applicator to stand upright when placed on a surface (e.g., a bathroom vanity surface), the body of the applicator may be shaped and sized so that its center of mass is located along the longitudinal axis of the body. In some embodiments, the center of mass is located in the lower one half of the body (e.g., closer to the proximal end than the tip), preferably within the grippable portion. The center of mass of a body may be easily determined by techniques known in the art. For instance, in cases of a single rigid body having a uniform density, the center of mass may be located at the geometric centroid of the body. The applicator may further exhibit a sufficient mass such that the user is able to easily grip, hold, and maneuver the applicator with control. Additionally, a sufficient mass may be perceived as more durable (e.g., not to be disposed of after use) and a higher quality. In some embodiments, the mass of the applicator is from about 10 g to about 125 g, from about 25 g to about 100 g, from about 25 g to about 75 g or any value from about 10 g to about 125 g or any range formed by any of the preceding values.

c. Dosing Indicators, Insertion Indicators and Other Visual Indicators

In some examples, an applicator may further comprise one or more visual indicators that delineate a feature of the applicator or distinguish one portion of the applicator from another. Visible indicators may also be provided to indicate where to hold the applicator, which end of the applicator is "up" or "down", and/or which surfaces of the applicator body to which the vaginal care composition should be applied. The visual indicator may be provided in a wide variety of forms. Some non-limiting examples include as a line, a micro-texture, a colored surface, a coating, a matte surface; a dull surface, a satin surface, a gloss surface, a micro-texture; text; graphics and combinations thereof, all of which may, for example, be printed on, coated on, or integrally formed with (e.g., in-molded) with the body.

Figure 21:
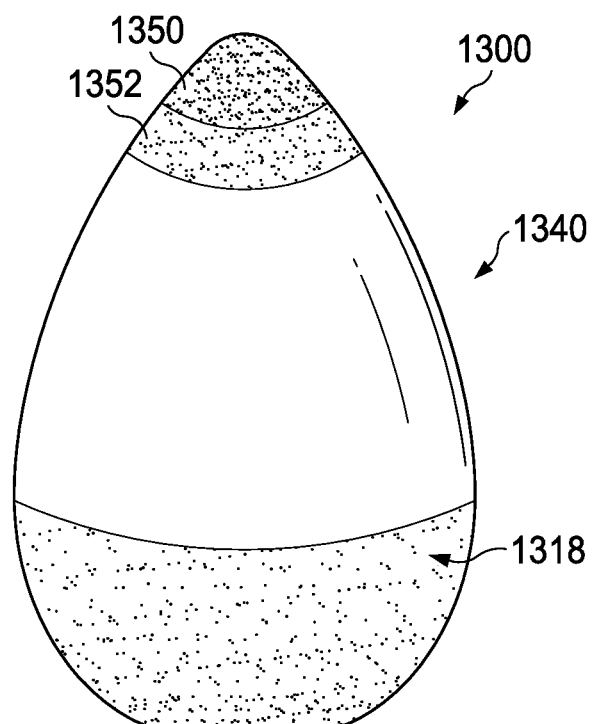
FIG. 21 is a perspective view of an eleventh example of an applicator, illustrating one embodiment of a dosing indicator and an insertion indicator (the rear view, not shown, being the same as the front view)

In some examples, the visual indicator is a dosing indicator that visually indicates to a user the surface of the body onto which the vaginal care composition is applied or an insertion indicator that visually indicates to user how far the body should be inserted into the vaginal introitus. The dosing indicator and/or the insertion indicator may form part of the insertion portion. Preferably, the dosing indicator is visually distinct from the insertion indicator. For example, FIG. 21 illustrates an applicator 1300 comprising two visual indicators in form of a dosing indicator 1350 and an insertion indicator 1352 disposed adjacent to the dosing indicator 1350, wherein the insertion indicator 1352 is disposed between the dosing indicator 1350 and the proximal end 1314. The dosing indicator and insertion indicator may be provided in wide variety of forms, including any of the forms previously described. For example, the dosing indicator 1350 may be provided in the form of a first color while the insertion indicator might be provided as a second color different from the first color. Or the dosing indicator 1350 may be provided in the form of a micro-texture while the insertion indicator 1352 is provided in the form of surface that has a visual appearance that is different from the dosing indicator 1350 (e.g., a glossy surface), whereby a user would be able to visually differentiate between dosing indicator 1350 and the insertion indicator 1352 and the insertion indicator 1352 and the intermediate portion 1340 or the grippable portion 1318. Referring again to FIGS. 11 and 12, dosing indicators 450 and 550 are illustrated. Dosing indicator 450 is provided in the form of a shallow ridge while dosing indicator 550 is shown (by way of stippling) as a micro-texture that covers a much larger surface area of the insertion portion. With reference again to FIGS. 13, 14 and 15, dosing indicators 650 (FIG. 13), 750 (FIG. 14) and 850 (FIG. 15) are illustrated. Dosing indicator 650 is provided in the form of printed leaves. Dosing indicator 750 is provided in the form of a raised (micro-texture) flower. Dosing indicator 850 is provided in the form of a printed pattern. The dosing indicator 850 is provided in a pattern that is substantially similar to or the same as the texture 819 provided in the grippable portion. While FIG. 21 illustrates the combination of a dosing indicator and an insertion indicator, merely a dosing indicator may be provided or the same visual indicator may be used as both a dosing indicator and an insertion indicator.

It will be appreciated that variations of the embodiments shown in FIGS. 11, 12, 13, 14, 15 and 21 may be provided. For example, different textures in the grippable portions may be employed or the grippable portion may be smooth (no texture). While dosing indicators may delineate the terminus or base of the insertion portion, it will be appreciated that the dosing indicators may extend beyond the terminus or base of the insertion portion. The dosing indicator and/or insertion indicator (as well as other visual indicators) may be printed on the body, in-molded with the body or be in the form of a coating applied to the body. The dosing indicator may have a surface area from about 500 $mm^2$ to about 4000 $mm^2$, or from about 700 $mm^2$ to about 3000 $mm^2$, or from about 700 $mm^2$ to about 2000 $mm^2$ or any value from about 500 $mm^2$ to about 4000 $mm^2$ or any range formed by any of the preceding values. The visual indicators may wholly or partially encircle the body of the applicator. In other embodiments, different colored material(s) may be used to form one or more portions of the applicator (e.g., blues, greens, and other cool temperature colors which connote beauty, cleanliness, and non-sexual) to differentiate one portion from another. For example, the insertion portion may comprise a first color while the grippable portion may comprise a second color that is different from the first color, and, optionally, the intermediate portion may comprise a third color that is different from the first color and the second color. Graphics (either printed or in-molded), drawn lines, patterns or visible particles within the materials may also be used as visual indicators to differentiate one portion of the applicator from another.

ii. Vaginal Care Compositions

The kit further comprises a vaginal care composition suitable for application to the vaginal introitus and, optionally, external vaginal tissues. In some examples, the vaginal care compositions are preferably non-irritating and substantially free of ingredients that are less suitable for application to these tissues. The vaginal care composition may be provided, for example, in the form of a spreadable gel, serum, lotion, paste or cream. Some non-limiting examples of vaginal care compositions which may be provided include, for example, vaginal moisturizing compositions (e.g., REPLENS®, NEOGYN®, VAGISIL® PROHYDRATE®, and ESTRACE®) and vaginal lubricant compositions (e.g., K-Y® UltraGel and Jelly, ASTROGLIDE®, ASTROGLIDE®, WET PLATINUM®, ALLATION® Gentle Moisture, and PURE ROMANCE® Just Like Me). In some examples, the vaginal care composition may comprise an estrogen agent and/or a progesterone agent. While the aforementioned compositions are suitable for use with the applicators and methods described herein, it is presently believed that vaginal care compositions in the form of oil-in-water emulsions with one or more additional ingredients are preferred. An oil-in-water emulsion may provide a sensorial feel that is light and non-greasy, but still delivers moisturization and lubricity without aesthetic negatives like stickiness or heavy residue. Further, the vaginal care compositions may further comprise one or more vaginal care agents. The vaginal care composition may comprise one or more water soluble ingredients.

In some examples, the vaginal care composition comprises water, one or more oils, and, optionally, one or more vitamins and/or pro-vitamins (e.g., a substance that may be converted to a vitamin by metabolic processes), one or more thickeners, one or more emulsifiers, one or more humectants, one or more lubricants (which may also be in the form of an oil), one or more moisturizers (which may also be in the form of an oil), one or more feel modifiers (e.g., particulates, powders and film forming agents), one or more preservatives and one or more pH adjusting agents. The vaginal care composition preferably provides a suitable viscosity, dry feel, moisturization/emolliency benefits, suitable lubricity and/or vaginal skin health benefits.

The vaginal care composition may comprise water in an amount greater than 50%, or greater than 60%, or from about 60% to about 90%, or from about 60% to about 80%, or from about 65% to about 75% by weight of the vaginal care composition. The water may provide a carrier for water soluble ingredients as well a moisturization benefit. The vaginal care composition may comprise one or more oils, including botanical oils, silicone oils and other oils. The vaginal care composition may comprise less than about 30%, or from about 1% to about 20%, or from about 5% to about 15%, or from about 10% to about 15% by weight of the vaginal care composition of oil(s). In some examples, the botanical oil is derived from one or more plant source materials, such as the leaf, root, bark, stem, flower or seed of a plant. The botanical oil may be a seed oil, a nut oil, a flower oil or a leaf oil. The botanical oil may comprise polyunsaturated fatty acids, preferably omega-3 (e.g., α-linolenic acid) and/or omega-6 fatty acids. The botanical oil may be a coconut oil, an evening primrose oil, a sunflower seed oil, a safflower oil and combinations thereof, all of which are enriched in omega-3 and/or omega-6 fatty acids. The botanical oil may provide an emolliency vaginal skin care benefit. The vaginal care composition may comprise from about 0.1% to about 2%, or from about 0.2% to about 1%, or from about 0.2% to 0.5% by weight of the vaginal care composition of botanical oil(s).

The vaginal care composition may comprise one or more vitamins and/or pro-vitamins for providing a vaginal skin health benefit. Some non-limiting examples include niacinamide, panthenol, vitamin B3, vitamin B5, vitamin E and derivatives thereof. The vaginal care composition may comprise from about 0.1% to about 7%, or from about 0.5% to about 5%, or from about 2% to about 4% by weight of the vaginal care composition of vitamin(s) and/or pro-vitamin(s).

The vaginal care composition may further comprise one or more silicone oils. Silicone oils are liquids comprising one or more polymerized siloxanes or silicone polymers (e.g., polysiloxanes, polydimethylsiloxanes (PDMS) and combinations thereof). The silicone oil may comprise dimethicone, dimethiconol (a high molecular weight silicone gum) and combinations thereof, one example being 1503 Fluid available from Dow Corning which comprises a combination of dimethicone and dimethiconol. The vaginal care composition may comprise from about 0.1% to about 4%, or from about 0.5% to about 3%, or from about 1% to 3% by weight of the vaginal care composition of silicone oil(s).

The vaginal care composition may comprise one or more humectants, such as glycerol. The humectants may also provide a moisturizing benefit. The humectant may be provided in an amount from about 5% to about 20%, or from about 5% to about 15%, or from about 8% to about 12% by weight of the vaginal care composition. Other humectants which may be provided include other polyhydroxy alcohols (e.g., sorbitol, propylene glycols, butylene glycols, pentylene hexylene glycols), polyethylene glycols, aloe vera in any of its forms, hyaluronic acid and combinations thereof.

The vaginal care composition may further comprise one or more solid micro-particles, such as silicone particulates/silicone powders, to impart desirable feel characteristics to the vaginal care composition. In some embodiments, the vaginal care composition comprises siloxane particles (e.g., polymethylsilsesquioxane) having an average particle size from about 1 μm to about 15 μm. The particles may be in the form of mono-disperse microspheres. The polymethylsilsesquixane particles are sometimes also referred to as silicone resins. Some non-limiting examples of polymethylsilsesquioxane particles include TOSPEARL® series from Momentive Performance Materials, Inc., including TOSPEARL® 2000, TOSPEARL® 145, TOSPEARL® 150, TOSPEARL® 1320 and the like. The solid micro-particles may have a melting temperature from about 25° C. to about 37° C. or about 28° C. to about 35° C. In addition to the small particle size and nature of the particles imparting a dry feel initially or when touched by the user (which is provides a beneficial initial experience), the melting point of the particles may facilitate additional lubricity in use upon melting, especially since the vaginal tissues of interest may be more likely to be close to standard body temperature (e.g., 37° C.) compared to, for example, some facial skin tissues. This may also facilitate the ease of spreading, rubbing or otherwise applying the vaginal care composition to the vaginal tissues of interest.

The vaginal care composition may further comprise one or more emulsifiers and/or one or more thickeners. Some non-limiting examples of emulsifiers include cationic surfactants, anionic surfactants, non-ionic surfactants, polyethylene glycol, polyethylene glycol polypropylene copolymers, alkyl glucosides, and fatty alcohols. Some non-limiting examples of thickeners include gums, starches, modified starches, clays, cross-linked water swellable polymers, cetearyl glucoside, cetearyl alcohol, behenyl alcohol, cetyl alcohol, stearyl alcohol, and polyacrylamide. The thickeners are provided in amounts to facilitate achieving the desired viscosity in combination with the other ingredients. The thickeners may be provided in an amount from about 1% to about 10%, or from about 2% to about 8%, or from about 4% to about 8% by weight of the vaginal care composition.

The vaginal care composition may preferably have a viscosity suitable for dispensing onto the applicator without dripping or runniness as the applicator is manipulated by a user prior to spreading the vaginal care composition about the vaginal introitus and/or external vaginal tissues. The vaginal care composition may also have a viscosity conducive to spreading onto the vaginal tissues of interest using the applicators described herein without undue effort. In some examples, it may be desirable for the vaginal care composition to be dispensable from a pump type dispenser. In some examples, the vaginal care composition may exhibit a viscosity of from about 2,000 cps to about 200,000 cps; in some examples, from about 5,000 cps to about 150,000 cps; and in some examples, from about 20,000 cps to about 90,000 cps or any value from about 2,000 cps to about 200,000 cps, or any range formed by any of the preceding values.

One non-limiting example of a suitable vaginal care composition is set forth below in Table 5.

TABLE 5

Example Composition Formulation

| Ingredient | % As Added |
| --- | --- |
| Water | 74.10 |
| Sodium Hyaluronate | 0.50 |
| Cocos Nucifera (Coconut) Oil | 0.20 |
| Helianthus Annuus (Sunflower) Seed Oil | 0.10 |
| Carthamus Tinctorious (Safflower) Seed Oil | 0.10 |
| Niacinamide | 3.00 |
| Glycerin | 10.00 |
| Stearyl Dimethicone | 1.00 |
| Disodium EDTA | 0.10 |
| Tocopheryl Acetate (Vitamin E) | 0.50 |
| Polymethylsilsesquioxane | 0.25 |
| Cetearyl Glucoside, Cetearyl Alcohol | 0.20 |
| Behenyl Alcohol | 0.80 |
| Sodium Benzoate | 0.18 |
| Sorbitan Caprylate | 0.20 |
| Cetyl Alcohol | 0.64 |
| Stearyl Alcohol | 0.96 |
| Peg-100 Stearate | 0.10 |
| Polyacrylamide(and)C13-14 Isoparaffin(and)Laureth-7 | 3.00 |
| Panthenol | 1.00 |
| Citric Acid | 0.48 |
| Sodium Citrate | 0.59 |
| Dimethicone and Dimethiconol | 2.00 |

In some examples, the vaginal care composition may be substantially free of retinol, retinyl esters, retinaldehyde, peptides, ethanol, sunscreens and sensates. In some examples, the composition may be substantially free of perfumes and pigments. In some examples, the composition may be substantially free of particulates for exfoliation. In such examples, the excluded particulates have an average particle size of from about 125 microns to about 700 microns or more. Examples of such particulates may include polyethylene terephthalate (PET) microbeads, crushed apricot kernel shells, salt crystals, sugar crystals, and crushed volcanic rock. It is believed the foregoing ingredients may either be irritating or present an unsatisfactory user experience in a vaginal care composition. In some examples, the vaginal care composition may be substantially free of the combination of carbomer and carbophil and other bioadhesives or mucoadhesive ingredients.

Referring back to FIG. 1, the vaginal care composition may be stored within a dispenser 104. The dispenser 104 may be any of a variety of dispensers suitable for dispensing, for example, a liquid, cream, lotion, etc. In some examples, the dispenser 104 may include a reservoir 142 for storing or containing the vaginal care composition and a hand pump 144 for drawing the vaginal care composition from the reservoir 142 and dispensing a dosage of the vaginal care composition from the dispenser 104. In one example, the dispenser may be a 30 mL Aptar Airless Micro Round Container (Part No: AA0EAA30012) and 0.3 mL Aptar Airless Micro Round Pump (Part No: AA00CD2732974A) from Aptar Group Inc. However, it will be appreciated that any suitable dispenser may be used. The amount of vaginal care composition applied to the insertion portion surface may be enough to cover the insertion portion surface but not so much that dripping of the vaginal composition from the insertion portion is induced. In some embodiments, the amount of the vaginal care composition applied to the insertion portion is from about 0.1 g to about 2 g, from about 0.2 g to about 1.2 g, or about 1 g. The dispenser 104 can be configured to regulate an amount of the vaginal care composition dispensed therefrom, such that the amount of the vaginal care composition released by the dispenser 104 may be a single dose consistent with the above-described ranges. In other embodiments, the amount dispensed per stroke of the pump may be such that multiple strokes are needed to dispense an amount consistent with the above-described ranges. For example, the pump may dispense from about 0.1 g to about 1 g or from about 0.1 g to about 0.5 g or from about 0.2 to 0.25 g per stroke.

In other examples, the vaginal care composition may be stored within a receptacle (not shown). The receptacle may be any of a jar, a bowl, a cup, or any of a variety of suitable receptacles, which may employ a screw-on lid or closure. In such examples, the insertion portion can be dipped into the receptacle to contact the vaginal care composition to transfer the vaginal care composition to a surface of the applicator. As such, the receptacle may define an opening that may have a width at least as wide as the maximum width $W_{max}$ of the insertion portion of the applicator.

In some examples, the applicator and the dispenser storing or containing the vaginal care composition may be packaged together as a unit for sale to a consumer. Some suitable packages may include boxes, cartons, and clamshell packages formed from plastic and/or a paper material. The kit may further include a container, such as, for example, a drawstring pouch or bag (e.g., 106), for storing one or more of the applicator and, optionally, the dispenser in between uses by a consumer. However, it will be appreciated that a container may be any of a variety of suitable containers or cases for storing one or more items associated with a kit. In some examples, the container may facilitate hygiene by maintaining cleanliness of the applicator between uses.

C. Methods of Use

The kits, applicators and vaginal care compositions may be used in a variety of ways. Referring again to FIG. 8, one method for treating vaginal dryness and/or vaginal atrophy, in accordance with one non-limiting embodiment, may include a female user grasping the applicator, depositing an amount of a vaginal care composition on at least a portion the insertion portion of the applicator, manipulating the applicator to administer the vaginal care composition to her vaginal introitus and, optional, external vaginal tissues such as at least one of the vulva, vestibule, labia majora, labia minora, external urogenital tract, with the insertion portion of the applicator such that at least a portion of the vaginal care composition thereon is transferred to the vaginal tissues of interest.

The methods described herein may be directed to and/or performed by women experiencing vaginal dryness and/or vaginal atrophy and/or suffering from a reduction in estrogen levels. Vaginal dryness may also be due to, for example, vaginitis, inflammation of the vagina due to thinning and shrinking of the tissues, sexual arousal disorder, menopause, drug (prescription or over the counter) induced vaginal dryness, dyspareunia, sexual pain disorder, pregnancy, breast feeding, hormone imbalance, anxiety and diabetes. In addition, the kits and vaginal care compositions may have non-medical uses for females in need of vaginal lubrication. Vaginal atrophy (sometimes referred to as atrophic vaginitis or vaginitis, vulvovaginal atrophy, or urogenital atrophy) may be characterized by thinning and shrinking of tissues as well as decreased lubrication, typically induced by a reduction in estrogen which happens naturally in perimenopausal, menopausal and post-menopausal women. Symptoms may include vaginal soreness, itching, dryness, and painful intercourse. In some examples, the female user is 40, 45, 50 or 55 years of age or older, experiencing a reduction in estrogen levels, suffering from vaginal atrophy, vaginal dryness, and/or is perimenopausal, menopausal or post-menopausal. It is believed that performance of the methods described herein using an applicator and vaginal care composition may provide the female user with an acute and/or a chronic reduction in one or more of vaginal dryness, pain during sexual intercourse, vaginal itching and vaginal irritation.

The method for treating vaginal dryness may include a female user holding or grasping the applicator and applying an amount of the vaginal care composition to at least a portion of the insertion portion, preferably the dosing surface, of the applicator. Alternatively, the applicator may be positioned on a surface (e.g., countertop) or held by a fixture to facilitate application of the vaginal care composition thereto without being grasped by the female user. In some examples, the method may further include applying an amount of the vaginal care composition to at least a portion of the insertion portion and the intermediate portion. The method may further include providing a single dose of the vaginal care composition on the applicator or a portion thereof (e.g., insertion portion 116 and/or the intermediate portion 140). The method may further include covering the lateral surface of the insertion portion, and optionally the intermediate portion, substantially in their entirety. This may be accomplished by the female user spreading the vaginal care composition about the surface of the insertion portion (e.g., using a fingertip or implement) or by moving the dispenser about the insertion portion as the vaginal care composition is dispensed therefrom. The vaginal care composition may be applied to or deposited on the insertion portion only or may be further applied to the intermediate portion, after which the body of the applicator may be manipulated so that the insertion portion and/or intermediate portion may contact the external vaginal tissues, including, for the example, one of the vulva, vestibule, labia majora, labia minora, and external urogenital tract, to administer the vaginal care composition thereto.

In some examples where the applicator comprises a dosing indicator and/or an insertion indicator, the female user may use those indicators as a guide as to where to deposit the vaginal care composition on the applicator (e.g., the dosing surface) or how far to insert the body into her vaginal introitus during use. In some examples, the dosing indicator may provide both visual cues to the female user (i.e., the same visual indicator functions as both a dosing indicator and an insertion indicator for the female user).

In some examples, the method may further include dispensing the vaginal care composition from the dispenser 104. In such examples, the vaginal care composition may be dispensed onto the insertion portion. The dispenser 104 may regulate an amount of the vaginal care composition released therefrom. The amount of the vaginal care composition released by the dispenser 104 may be the single dose sufficient for covering the insertion portion or a lesser amount such that multiple actuations (e.g., 2-4) of the dispenser are needed to provide a suitable amount.

In another example, the vaginal care composition can be stored within a receptacle (not shown), such as a jar or can. The insertion portion can be dipped into the receptacle to contact the vaginal care composition for application thereon. While the method has been described in association with use of the applicator, it will be appreciated that in some examples, a method for treating female genital dryness may include applying a vaginal care composition to at least one digit (e.g., finger or thumb) of a female user and administering the vaginal care composition to the vaginal introitus and, optionally, the external vaginal tissue using her at least one digit. As such, the receptacle may also define an opening having a width at least as wide as the at least one digit of the user.

To treat female genital dryness and/or vaginal atrophy, a female user may grasp or hold the applicator and manipulate the applicator to administer the vaginal care composition to her vaginal introitus and, optionally, at least one of the vulva, vestibule, labia majora, labia minora, external urogenital tract, using the insertion portion such that at least a portion of the vaginal care composition thereon is transferred to the vaginal tissue. The female user may be seated, standing, laying down, squatting, or have one leg supported by a surface during manipulation of the applicator. The female user grasps the grippable portion of the applicator with 2, 3, 4, or 5 fingertips, preferably with the pads of the fingertips (one example being shown in FIG. 8). The female user may grasp the applicator using only her fingertips, and not her fingernails or the palm of her hand or lower knuckles in order to provide better control over manipulation of the applicator. In some examples, the grippable portion is deformable (e.g., the material used to form it has a Shore A hardness or the grippable portion has a peak compressive force) so that the female user may slightly compress the grippable portion, for example by 0.5 mm to about 2 mm, using her fingertip pads. This permits the female user to more easily grasp the applicator and ergonomically manipulate the applicator in a variety motions to administer the vaginal care composition to the vaginal introitus and, optionally, external vaginal tissues. In those the embodiments where the applicator is rotationally symmetrical, the female user may grasp the applicator from any orientation and manipulate the applicator in a wide variety of manners (which is useful when the female user is in one of a variety of positions, such a seated, standing or laying down) without accounting for the orientation of the applicator within her hand. This provides easy and quick performance of the method of treatment. The female user may insert the applicator into her vaginal introitus a distance of about 25 mm or less to apply the vaginal care composition to her introitus.

The female user may manipulate the applicator in variety manners. The female user may insert the insertion portion into her vaginal introitus using gentle handle pressure (e.g., until slight resistance to insertion is noticed by the user) so as to not over insert the body thru the vaginal introitus. The body of the applicator is preferably only inserted far enough to treat the vaginal introitus without discomfort. The insertion portion is inserted only so far as is comfortable to avoid pain or tearing or bleeding from the delicate tissues. The female user may insert the body into the vaginal introitus a distance of 40 mm, 35 mm, 30 mm, 25 mm or less, or from about 30 mm to about 5 mm or from about 25 mm to about 10 mm. In some examples, the fingertip offset distance when the female user grasps the applicator is from about 30 mm to 65 mm, or from about 30 mm to about 60 mm, or from about 30 mm to about 55 mm. Without wishing to be bound by theory, it is believed that consumers will be adverse to self touch and soiling their fingers with bodily fluid and/or the vaginal care composition. As such, applicators designed to be gripped with the fingertip offset distances described above will result in the insertion portion being inserted minimally into the introitus during use. In some examples, the width of the applicator at a longitudinal distance of 25 mm from the tip of the insertion portion is from about 15 mm to 45 mm, or from about 20 mm to about 40 mm, or from about 25 mm to about 35 mm. This may further help limit the insertion of the applicator into the introitus and for a cone-shaped insertion portion provide a slope to the outer surface of the insertion portion that accommodates a wide variety of vaginal introitus and vaginal tissue geometries. In some examples, the maximum width of the applicator where the female user grasps the applicator is from about 20 mm to 70 mm, or from about 25 mm to about 60 mm, or from about 30 mm to about 55 mm. These widths allow for easy grasping and manipulation of the applicator with a single hand during use.

In some examples, the shape of the body (e.g., the maximum width $W_{max}$) limits the insertion depth of the body when gentle hand pressure is applied to the applicator. Preferably, the tip of the insertion portion is not inserted as far as the middle or upper region of the vaginal canal by the female user. In some examples, the tip of the insertion portion is inserted no further than the lower region of the vaginal canal. It is believed that at least some female users may find this method less intimidating and/or more simple and convenient, thereby encouraging long term habit adoption and compliance. The body of the applicator may then be retracted to administer any remaining vaginal care composition thereon (and/or to spread some of the vaginal care composition applied to the vaginal introitus) to the external vaginal tissues, such as labia minora, labia majora, the clitoris, the perineum, the urogenital tract, etc.

Figure 22:
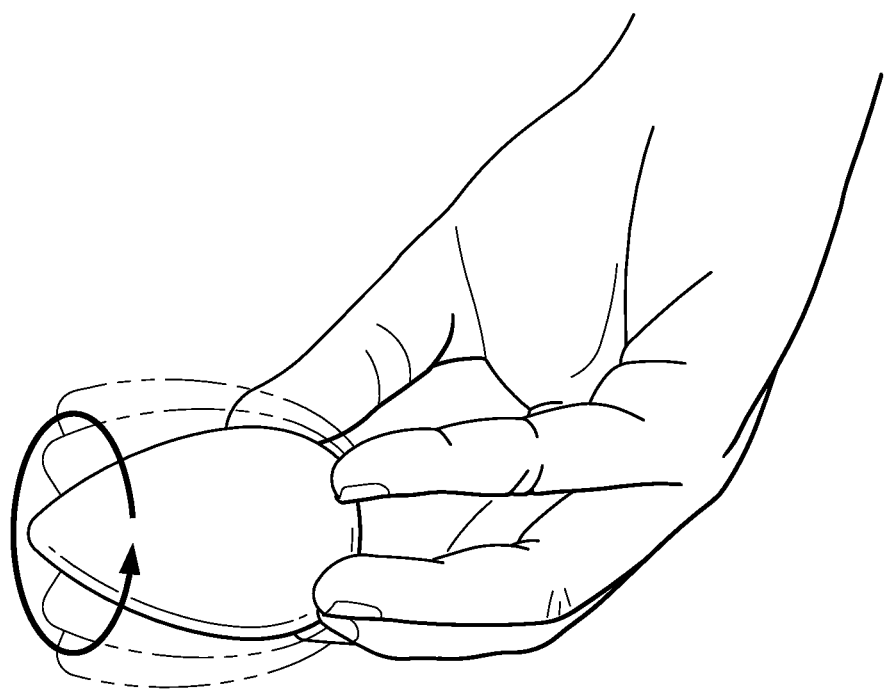
FIG. 22 is a schematic illustration of a method of using the applicator of FIG. 2.
Figure 23:
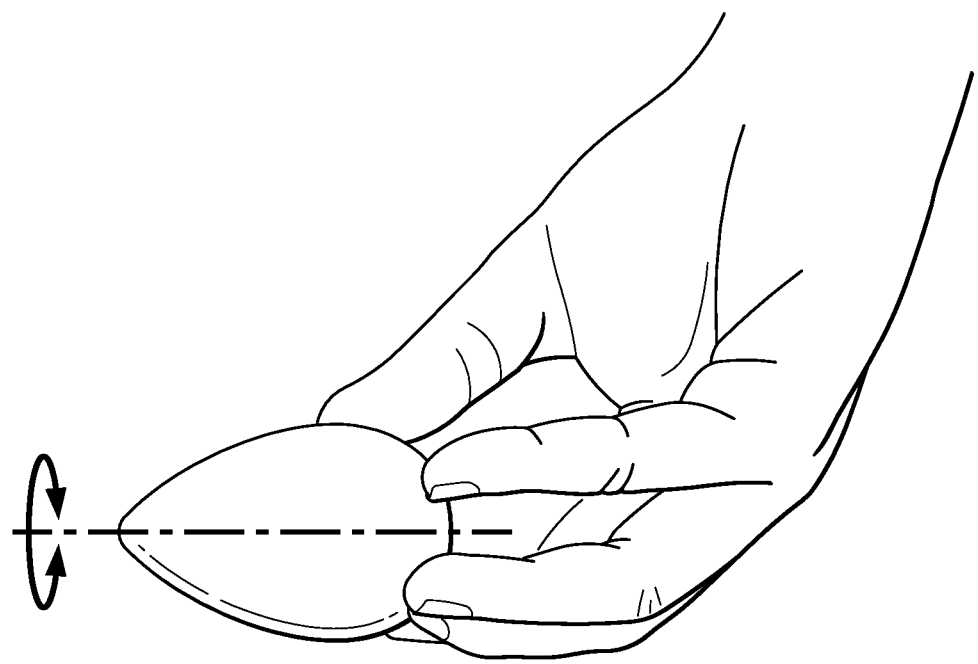
FIG. 23 is a schematic illustration of another method of using the applicator of FIG. 2.
Figure 24:
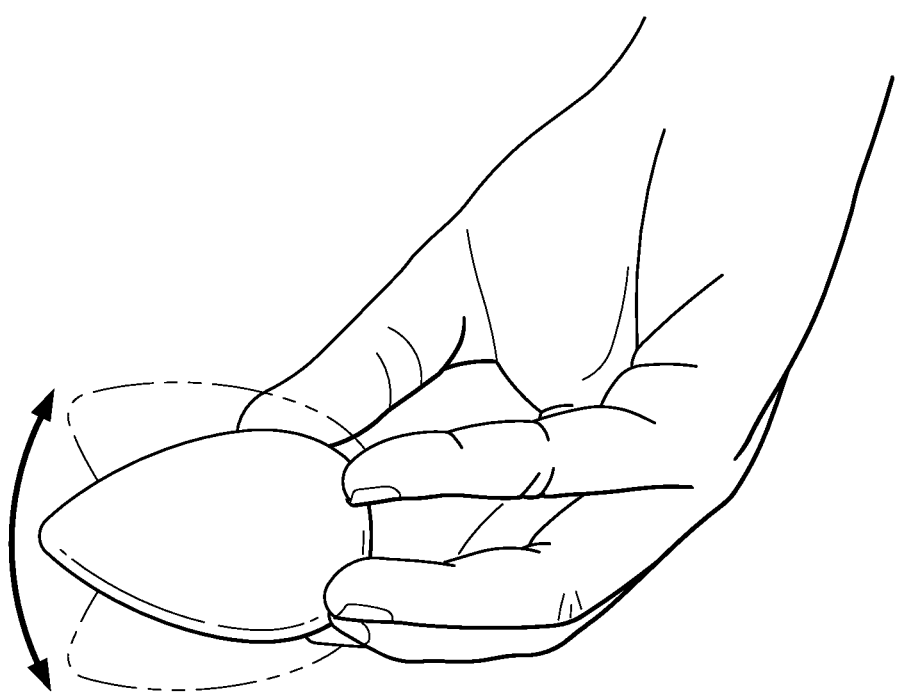
FIG. 24 is a schematic illustration of still another method of using the applicator of FIG. 2.

Referring to FIGS. 22 and 23, for example, the female user may manipulate the applicator by inserting the body into the vaginal introitus and rotating the body of the applicator using her wrist, retracting the body from the vaginal introitus and then swiping the body along the external vaginal tissues. The tip of the insertion portion of the applicator may trace a generally circular or oval pattern as shown, for example, in FIG. 22. In addition or alternatively, the applicator may be rotated back and forth about the longitudinal axis as shown, for example, in FIG. 23. In addition, or alternatively, the female user may manipulate the body by pivoting the body up and down about the wrist or fingertips shown, for example, in FIG. 24. The female user may further manipulate the applicator by swirling, pivoting, swiping, rotating, revolving or a gliding motion thru use of her fingertips or wrist. In certain methods, the aforementioned manipulations may be applied to the vaginal introitus and/or the external vaginal tissues. In certain methods, a combination of the aforementioned motions may be performed.

In some examples, the female user may administer the vaginal care composition to the vaginal tissues of interest for a period of time from about 1 second to about 40 seconds or about 1 second to about 30 seconds or from about 1 second to about 15 seconds or any range formed by any of the preceding values. A short administration time is desirable for providing a method that is convenient and quick to complete. Since the methods described herein are for treatment of vaginal dryness and/or vaginal atrophy and typically involve short administration times, use of the applicator may be less than needed for sexual arousal to occur.

Since the experience of both the applicator and vaginal care composition may be useful for encouraging long term habit adoption by a female user for both acute and chronic treatment of vaginal dryness and/or vaginal atrophy, the female user may use the applicator to apply the vaginal care composition on a regular basis versus as a mere precursor to sexual intercourse. For example, the method of use may not be immediately followed by sexual intercourse. Further, sexual intercourse may not even occur within 6, 12 or 24 hours of the administration of the vaginal care composition since application of the vaginal care composition is not necessarily linked to the timing of sexual intimacy. With respect to frequency of administration, in some examples, the method may be performed by a female user at least twice per week or three, four, five, six times per week or more for a period of at least 4 weeks or 8 weeks or 12 weeks or more. In other instances, the method may be performed daily for a period of at least 4 weeks or 8 weeks or 12 weeks or more. In some instances, the female user may perform the method for 6, 8, 10, 12 months or more. The method may be performed by a female user at about the same time each day or following a daily ritual activity in order to facilitate habit adoption and habit compliance. For example, the female user may perform the method in the morning, as part of a routine (e.g., after showering). Similarly, a female user may perform the method in the evening before bed or at any other time convenient to the female user.

The methods may further include cleaning the applicator so that the applicator may be reused at a later time to repeat administration of the vaginal care composition. In some embodiments, the applicator is sufficiently durable and/or hygienic so that the female user may safely repeat the method 2, 5, 10, 20, 30, 40, or 50 times or more using the same applicator. While it is desirable for the applicator to be durable, it is appreciated that daily use may result in some degradation or soiling over time and require replacement of the applicator by a new or fresh applicator after 2, 3, 4 weeks or more of use. The new or fresh applicator may be obtained separately or as part of a new kit that includes a new applicator and dispenser comprising a vaginal care composition. The female user may use from about 6, 12, 18 or more fresh or new kits per year. In some examples, the applicator may be rinsed, sprayed or immersed in a liquid and/or wiped with a substrate to remove any residual vaginal care composition or bodily fluids. The substrate may be a woven or non-woven material which may be washed (by hand or in a washing machine) for cleanliness. The substrate may single use and disposable. The substrate and/or cleaning liquid may be packaged together with the kit if desired or distributed separately. The cleaning liquid may comprise water and, optionally, one or more adjuncts such as, for example, a soap or other surfactant. The applicator may be immersed in a container containing the cleaning liquid or merely rinsed or immersed in tap water, for example. Following the rinsing, spraying or immersion step, the applicator may be dried with a substrate or appliance (e.g., hair dryer) or left to air dry, and the applicator stored in a protective in a reusable container/package (e.g., the drawstring pouch shown in FIG. 1) for cleanliness until the next use. The protective container may be closed by a zipper, drawstring, magnets, Velcro or any other closure mechanisms known in the art. The applicator, protective container and dispenser may be travel sized so that they can be stored in a purse if desired. In some examples, the cleaning step may be performed prior to application of the vaginal care composition to the applicator, subsequent to administration of the vaginal care composition to desired vaginal tissue, or both. In other examples, however, it will be appreciated that an applicator may be disposable or intended for a single use.

D. Test Procedures i. Tensile Properties of the Applicator

Peak Force Tip and Peak Force Lateral Surface properties of the applicator are measured on a constant rate of extension tensile tester with computer interface (a suitable instrument is the MTS Insight using Testworks 4.0 Software, as available from MTS Systems Corp., Eden Prairie, MN) using a load cell for which the forces measured are within 5% to 95% of the limit of the cell. Both the movable (upper) and stationary (lower) fixture are fitted with light weight circular platens, the lower being 75 mm in diameter and the upper 25 mm in diameter. The platens are adjusted with calibrated blocks (traceable to NIST or other standards agency) to be orthogonal to the pull axis of the tensile tester. All testing is performed in a conditioned room maintained at about 23° C.±2C.° and about 50%±2% relative humidity.

Program the tensile tester for a compression test after an initial gage length adjustment. Lower the upper platen at 10 mm/min until the platen touches the applicator with a force of 0.2 gf. Set the adjusted gage length to zero. Lower the platen at 10 mm/min for an additional 2.0 mm followed by a hold for 10 sec, then raise the platen at 10 mm/min for 2.0 mm. Force (N) and displacement (mm) data is recorded at a rate of 100 Hz throughout the experiment. Return the crosshead to its starting position.

Applicators are conditioned at about 23° C.±2C.° and about 50%±2% relative humidity for at least two hours before testing. Raise the crosshead of the tensile tester. Place the applicator onto the lower platen such that the tip is orthogonal to the upper platen and lower the upper platen to approximately 3 mm above the tip. Zero the crosshead and load cell, and begin the program and record the data. Construct a Force (N) verses Displacement (m) curve of the data. From the curve read the maximum peak force and record as Peak Force (N) to the nearest 0.01N. The Peak Tip Force is the average of this Peak Force measured on five replicate applicators to the nearest 0.01N.

Rotate the sample 90 degrees relative to the lower platen and then rotate the applicator about the axis parallel to the lower platen to center the largest dimension about said axis between the lower and the upper platens. Lower the upper platen to within 3 mm of the applicator sample. Zero the crosshead and load cell, and begin the program and record the data. Construct a Force (N) verses Displacement (m) curve of the data. From the curve read the maximum peak force and record as Peak Force (N) to the nearest 0.01N. The Peak Force Lateral Surface is the average of this Peak Force measured on five replicate applicators to the nearest 0.01N.

ii. Applicator Surface Texture Method

In the Applicator Surface Texture Method, the areal surface topology of the applicator is measured using optical profilometry. The 3D surface data are processed to measure the microscale areal surface roughness parameters Sq (root mean square height), as described in ISO 25178-2:2012, which characterize the surface roughness over a given surface area. All sample preparation and testing is performed in a conditioned room maintained at about 23±2° C. and about 50±2% relative humidity, and samples are equilibrated in this environment for at least 24 hours prior to testing.

Sample Preparation

Five new substantially similar replicate applicator samples are selected for analysis.

3D Surface Image Acquisition

Three-dimensional (3D) surface topography images of the applicator area of interest (e.g. tip, grippable portion) are recorded using an optical 3D surface topography measurement system (a suitable optical 3D surface topography measurement system is the MikroCAD Light instrument commercially available from LMI Technologies Inc., Vancouver, Canada, or equivalent). The system includes the following main components: a) a Digital Light Processing (DLP) projector with direct digital controlled micro-mirrors; b) a CCD camera with at least a 1600×1200 pixel resolution; c) projection optics adapted to a measuring area of at least 5 mm×4 mm; d) recording optics adapted to a measuring area of 5 mm×4 mm; e) a table tripod based on a small hard stone plate; f) a blue LED light source; g) a measuring, control, and evaluation computer running surface texture analysis software (a suitable software is MikroCAD software with MountainsMap technology, or equivalent); and h) calibration plates for lateral (xy) and vertical (z) calibration available from the vendor.

The optical 3D surface topography measurement system measures the surface height of a sample using the digital micro-mirror pattern fringe projection technique. The result of the measurement is a 3D image of surface height (defined as the z-axis) versus displacement in the horizontal (xy) plane. The system has a field of view of 5×4 mm with an xy pixel resolution of approximately 3 microns, and a height resolution of 0.1 microns, with a height range of +/−2 mm.

The instrument is calibrated according to manufacturer's specifications using the calibration plates for lateral (xy plane) and vertical (z-axis) available from the vendor.

The applicator sample is placed on the table such that the region to measure is oriented horizontally beneath the camera. Analysis regions are selected such that the curvature within the region imaged is minimized. Each analysis region excludes any visually obvious macroscopic features such as an: opening, ridge, groove, edge, or corner.

A 3D surface topology image of the sample is collected by following the instrument manufacturer's recommended measurement procedures, which may include focusing the measurement system and performing a brightness adjustment. No pre-filtering options are used. The collected height image file is saved to the evaluation computer running the surface texture analysis software.

3D Surface Image Analysis

The 3D surface topography image is opened in the surface texture analysis software. The following filtering procedure is then performed on each image: 1) a 5×5 pixel median filter to remove noise; 2) a 5×5 pixel mean filter to smooth the surface; and 3) a Gaussian filter (according to ISO 16610-61) with a nesting index (cut-off) of 0.8 mm without utilizing end effect correction to flatten the surface; 4) Threshold and remove the heights corresponding to a material ratio value of less than 2% and a material ratio of greater than 98% to remove outliers. The Areal Material Ratio (Abbott-Firestone) curve, described in the ISO 13565-2: 1996 standard and extrapolated to surfaces, is the cumulative curve of the surface height distribution histogram versus the range of surface heights. A material ratio is the ratio, given as a %, of the intersecting area of a plane passing through the surface at a given height to the cross sectional area of the evaluation region.

This filtering procedure produces the surface from which the Sq values, as described in ISO 25178-2:2012, are calculated. Record the surface roughness values for Sq to the nearest 0.1 μm. Repeat this procedure over the same area of interest for the remaining replicate samples. The surface texture is the average of the 5 replicate Sq measures to the nearest 0.1 μm.

iii. Absorbency

Absorbency is measured as the gravimetric fluid uptake of an applicator sample submerged into a test fluid. Prepare a 0.042% w/v of Tritan X-100 solution, (reagent grade Sigma-Aldrich, or equivalent) in purified water (e.g. water from a Mill-iQ system) as the test fluid. The fluid's surface tension is tested and the result should be 32 dyne±1 dyne. All testing is performed in a conditioned room maintained at about 23° C.±2C.° and about 50%±2% relative humidity and samples are conditioned under these conditions for 2 hours before testing.

Measure the mass of the applicator and record as the Dry Mass to the nearest 0.0001 g. Place 400 mL of test fluid into a 500 mL beaker. If needed, the fluid level and beaker can be chosen such that the applicator can be completely submerged without overflowing the beaker. Soak the sample for 5.0 min±0.1 min. With tongs remove the sample and place onto a wire rack with the tip directed downward. After 1.0 min±0.1 min, place the sample into a tared weigh boat and measure the mass of the sample. Record the Wet Mass to the nearest 0.0001 g. The Absorbency (%) is calculated as (Wet Mass-Dry Mass)/Dry Mass and recorded to the nearest 0.01%. Repeat the measure for a total of five samples. Calculate the arithmetic average of the five results and report to the nearest 0.01%.

iv. Viscosity

The viscosity of samples is measured using Brookfield RV viscometer fitted with a helipath T-bar spindle type T-A. The viscometer is leveled, setup and calibrated according to the manufacturer's standards. The viscometer speed (RPM) is selected to ensure the measured viscosity is within the manufactures recommended settings.

Samples are stored in sealed glass jars with an opening and internal diameter of at least 40 mm and filled to a height of at least 50 mm with care taken to avoid entrapped air bubbles. Centrifugation may be used to help remove entrained air. Sample jars are equilibrated at 23° C.±2° C. and about 50%±2% relative humidity for at least 24 hours prior to measurement.

Viscosity is measured at 23° C.±2° C. and about 50%±2% relative humidity by placing the uncapped sample jar under the viscometer and lowering the viscometer until the tip of the t-bar touches the surface of the sample. The descending helipath is turned on and a timer started once the cross-bar of the t-bar touches the surface of the sample. For 1 minute, a reading is taken every 10 seconds. The viscosity is the arithmetic average of the viscosities recorded. Care is taken to ensure the t-bar does not touch the glass jar.

Further Non-Limiting Description of the Disclosure

The following numbered paragraphs constitute a further non-limiting description of the disclosure in a form suitable for appending to the claim section if later desired.

A. An applicator for treating vaginal dryness, comprising:
  a. a hand-held body, optionally an elongate hand-held body, for applying a composition to the vagina, preferably to the vaginal introitus and/or external vaginal tissues, wherein the hand-held body comprises a rounded insertion portion and a grippable portion,
  wherein the applicator preferably has an overall length L1 from about 20 mm to 90 mm, preferably from about 30 mm to about 80 mm, more preferably from about 40 mm to 70 mm; and a maximum width Wmax from about 20 mm to about 80 mm, preferably from about 25 mm to about 70 mm, more preferably from about 30 mm to about 50 mm.

B. A system for treating vaginal dryness, comprising:
  a. an applicator for treating vaginal dryness, the applicator comprising a hand-held body, optionally an elongate hand-held body, for applying a composition to the vagina, preferably to the vaginal introitus and/or external vaginal tissues, wherein the hand-held body comprises an insertion portion, preferably an insertion portion having a rounded tip, and a grippable portion, wherein the insertion portion is shaped and configured to hold the composition, the composition preferably having a viscosity of from about 2,000 cps to about 200,000 cps, more preferably from about 5,000 cps to about 150,000 cps, even more preferably from about 20,000 cps to about 90,000 cps,
  wherein the applicator preferably has an overall length L1 from about 20 mm to 90 mm, preferably from about 30 mm to about 80 mm, more preferably from about 40 mm to 70 mm; and a maximum width Wmax from about 20 mm to about 80 mm, preferably from about 25 mm to about 70 mm, more preferably from about 30 mm to about 50 mm.

C. A method of treating an applicator for treating vaginal dryness comprising:
  a. applying a vaginal care composition, preferably an effective amount, more preferably from about 0.1 g to about 2 g of the vaginal care composition, even more preferably from about 0.5 g to about 1 g of the vaginal care composition, most preferably about 1 g of the vaginal care composition, from a dispenser storing or containing the vaginal care composition to an insertion portion of the applicator body,
  b. subsequently inserting the applicator into the vagina, preferably wherein the vagina is treated substantially without digital application of the vaginal composition to the vagina, and
  c. optionally repeating these steps at least twice per week for a period of at least 2 weeks or 4 weeks.

D. A method for treating vaginal dryness, comprising:
  a. a female user suffering from vaginal dryness grasping an applicator, the applicator comprising a hand-held body, optionally an elongate hand-held body, wherein the hand-held body comprises an insertion portion having a rounded tip and a grippable portion;
  b. the female user depositing a vaginal care composition on the insertion portion, preferably on at least a portion of the outer surface of the insertion portion;
  c. the female user inserting the applicator into the vagina, preferably into the vaginal introitus and/or external vaginal tissues, a distance of about 35 mm or less, preferably 30 mm or less, more preferably 25 mm or less; and d. preferably applying the vaginal care composition to the vagina, more preferably to the vaginal introitus and/or external vaginal tissues.

E. A kit for treating vaginal dryness, comprising:
  a. a dispenser storing or containing a composition optionally comprising an oil in water emulsion, preferably wherein the dispenser defines an opening having a width at least as wide as the maximum width, $W_{max}$, of the hand-held applicator;
  b. an applicator comprising a hand-held body, optionally an elongate hand-held body, for applying the composition to the vagina, preferably to the vaginal introitus and/or external vaginal tissues, wherein the hand-held body comprises an insertion portion, optionally a tapered insertion port, the insertion portion preferably having a rounded tip, tapered insertion portion, and a grippable portion that is preferably located adjacent the proximal end, wherein the applicator is preferably separate from the dispenser and wherein the applicator preferably has an overall length L1 from about 20 mm to 90 mm, preferably from about 30 mm to about 80 mm, more preferably from about 40 mm to 70 mm; and a maximum width Wmax from about 20 mm to about 80 mm preferably from about 25 mm to about 70 mm, more preferably from about 30 mm to about 50 mm; and
  c. optionally, a container for storing or containing the hand-held applicator in between uses.

F. The applicator, system, method, or kit according to any one of the preceding paragraphs, wherein the hand-held body comprises a polyurethane, a thermoplastic elastomer, a cross-linked silicone rubber, or a combination thereof, optionally the polyurethane, thermoplastic elastomer or cross-linked silicone rubber has a Shore A hardness from about 5 to about 30.

G. The applicator, system, method, or kit according to any one of the preceding paragraphs, wherein the hand-held body comprises a cross-linked silicone rubber, preferably a medical grade cross-linked silicone rubber.

H. The applicator, system, method, or kit according to any one of the preceding paragraphs, wherein the insertion portion is smooth.

I. The applicator, system, method, or kit according to any one of the preceding paragraphs, wherein the vaginal care composition is substantially free of an estrogen agent, a progesterone agent, or a combination thereof.

J. The applicator, system, method, or kit according to any one of the preceding paragraphs, wherein the hand-held body has a longitudinal axis and/or a proximal end.

K. The applicator, system, method, or kit according to any one of the preceding paragraphs, wherein the insertion portion has a tip opposite the proximal end.

L. The applicator, system, method, or kit according to any one of the preceding paragraphs, wherein the applicator has a maximum width, $W_{max}$, located in the lower one half of the body, preferably the applicator has a taper from the maximum width, Wmax, to the insertion portion, more preferably the applicator has a continuous taper from the maximum width, Wmax, to the insertion portion.

M. The applicator, system, method, or kit according to any one of the preceding paragraphs, wherein at least 60%, 70%, 80%, 90%, 95% or 100% of the bulk volume of the applicator is solid volume.

N. The applicator, system, method, or kit according to any one of the preceding paragraphs wherein the applicator is substantially free or devoid of moving parts.

O. The applicator, system, method, or kit according to any one of the preceding paragraphs, wherein the insertion portion is cone-shaped.

P. The applicator, system, method, or kit according to any one of the preceding paragraphs, wherein the hand-held body is non-electrical.

Q. The applicator, system, method, or kit according to any one of the preceding paragraphs, wherein the insertion portion further comprises a dosing indicator that preferably delineates a dosing surface, optionally wherein the dosing indicator is printed on the body, comprises a texture in the form of a ridge or a groove, comprises a color that is different from a color of the body, is in-molded with the body, or comprises a colored surface, a coating, text, a texture, optionally a microtexture, or a graphic applied to or integrally formed with the body.

R. The applicator, system, method, or kit according to any one of the preceding paragraphs, wherein the grippable portion comprises a texture, optionally the texture is disposed adjacent to the proximal end, the texture partially or wholly encircles the body, the texture has a maximum height or a maximum depth from about 0.1 mm to about 4 mm, or about 0.25 mm to about 3 mm, or about 1 mm to about 2 mm, the texture is in the form of a plurality of ridges, a plurality of grooves, a plurality of dimples, a plurality of flowers or a plurality of leaves, or the texture is provided as a repeating pattern.

S. The applicator, system, method, or kit according to any one of the preceding paragraphs, wherein the applicator body is substantially free or devoid of a chamber for storing or containing a flowable composition.

T. The applicator, system, method, or kit according to any one of the preceding paragraphs, wherein the dosing surface of the applicator has a surface area from about 500 mm2 to about 4,000 mm2, or about 700 mm2 to about 3,000 mm2, or about 700 mm2 to about 2,000 mm2.

U. The applicator, system, method, or kit according to any one of the preceding paragraphs, wherein the insertion portion further comprises an insertion indicator that indicates to a user how far the applicator should be inserted into a vaginal introitus, optionally the insertion indicator is distinct from the dosing indicator, is disposed adjacent thereto, and/or is located closer to the proximal end than the dosing indicator.

V. The applicator, system, method, or kit according to any one of the preceding paragraphs, wherein the dosing indicator and the insertion indicator partially or wholly encircle the body.

W. The applicator, system, method, or kit according to any one of the preceding paragraphs, wherein the cross-sectional shape of the body at the base of the insertion portion is circular or ovoidal.

X. The applicator, system, method, or kit according to any one of the preceding paragraphs, wherein the applicator body consists essentially of single material, preferably wherein the single material is a cross-linked silicone rubber.

Y. The applicator, system, method, or kit according to any one of the preceding paragraphs, wherein the applicator body is formed by injection molding or casting, preferably the body is devoid of part lines within the insertion portion.

Z. The applicator, system, method, or kit according to any one of the preceding paragraphs, wherein the body has a circumferential part line located outside the insertion portion, preferably the part line is located at or near the maximum width Wmax.

AA. The applicator, system, method, or kit according to any one of the preceding paragraphs, wherein the applicator is not phallic shaped.

BB. The applicator, system, method, or kit according to any one of the preceding paragraphs, wherein the proximal end further comprises a substantially planar portion and wherein the applicator preferably stands upright when placed on flat surface.

CC. The applicator, system, method, or kit according to any one of the preceding paragraphs, wherein the center of mass of the applicator is located along its longitudinal axis and in the lower one half of the body.

DD. The applicator, system, method, or kit according to any one of the preceding paragraphs, wherein the vaginal care composition is stored in a dispenser and wherein the dispenser comprises a pump that regulates the amount of the vaginal care composition dispensed therefrom to between about 0.1 g and 2 g per actuation of the pump.

EE. The applicator, system, method, or kit according to any one of the preceding paragraphs, wherein the applicator has a rotational symmetry about its longitudinal axis thru a rotation of 45°, 90°, 135°, 180°, 225°, 270°, 315° or 360°.

FF. The applicator, system, method or kit according to any of the preceding paragraphs, wherein the body is homogeneous.

GG. The applicator, system, method or kit according to any of the preceding paragraphs, wherein the body is integrally constructed from two or more materials or parts.

HH. The applicator, system, method or kit according to any of the preceding paragraphs, wherein the insertion portion has a length L2 from about 10 mm to about 40 mm that defines a location of a base of the insertion portion and a width W2 from about 10 mm to about 40 mm at the base of the insertion portion.

II. The applicator, system, method, or kit according to any one of the preceding paragraphs, wherein the applicator body exhibits one or more of:
  i) a Peak Force (Tip) from about 0.1N to about 40N, or from about 0.2N to about 10N, or about 0.3N to about 5N; or
  ii) a Peak Force (Lateral Surface) from about 0.4N to about 90N, or from about 0.7N to about 20N, or about 0.9N to about 10N; or
  iii) an absorbency less than 10%, or from about 0.01% to about 2% or from about 0.05% to about 1%.

JJ. The applicator, system, method, or kit according to any one of the preceding paragraphs, wherein the applicator body further comprises a grippable portion adjacent the proximal end, the grippable portion having a length L4 from about from about 5 mm to about 65 mm, preferably from about 10 mm to about 50 mm, more preferably from about 20 mm to about 40 mm.

KK. The applicator, system, method, or kit according to any one of the preceding paragraphs, wherein the maximum width $W_{max}$ is disposed a length L3 from the tip and wherein the length L3 is from about 35 mm to about 90 mm.

LL. The applicator, system, method, or kit according to any one of the preceding paragraphs, wherein a ratio of the length L3 to the length L4 of the grippable portion is from about 1:1 to about 9:1, preferably from about 1:1 to about 4:1, more preferably from about 1.5:1 to about 3:1.

MM. The applicator, system, method, or kit according to any one of the preceding paragraphs, wherein the grippable portion further comprises a texture in the form of a one or more protrusions, one or more recesses or a combination thereof.

NN. The applicator, system, method, or kit according to any one of the preceding paragraphs, wherein the applicator further comprises an intermediate portion disposed between the insertion portion and the grippable portion, optionally the intermediate portion has a longitudinal length L5 from about 25 mm to about 80 mm, or 25 mm to about 70 mm, or from about 30 mm to about 60 mm, optionally the intermediate portion is smooth.

OO. The applicator, system, method, or kit according to any one of the preceding paragraphs, wherein a ratio of the overall length L1 of the applicator to the maximum width $W_{max}$ of the applicator is from about 1:2 to about 5:1 or from about 1:1 to about 4:1.

PP. The applicator, system, method, or kit according to any one of the preceding paragraphs, wherein the applicator tapers from the maximum width $W_{max}$ to the tip and the applicator tapers from the maximum width $W_{max}$ to the proximal end.

QQ. The applicator, system, method, or kit according to any one of the preceding paragraphs, wherein the vaginal care composition comprises one or more oils, preferably selected from the group consisting of silicone oils, botanical oils, or combinations thereof.

RR. The applicator, system, method, or kit according to any one of the preceding paragraphs, wherein the silicone oil comprises a polydimethylsiloxane.

SS. The applicator, system, method, or kit according to any one of the preceding paragraphs, wherein the botanical oils are selected from coconut oil, evening primrose oil, sunflower seed oil, safflower oil, or combinations thereof.

TT. The applicator, system, method, or kit according to any one of the preceding paragraphs, wherein the composition or vaginal care composition further comprises one or more emulsifiers, one or more vitamins or pro-vitamins, preferably vitamin E, vitamin B3, vitamin B5, panthenol or combinations thereof, a humectant, or a combination thereof.

UU. The applicator, system, method, or kit according to any one of the preceding paragraphs, wherein the vaginal care composition further comprises water in an amount greater than 60% by weight of the vaginal care composition.

VV. The applicator, system, method, or kit according to any one of the preceding paragraphs wherein the vaginal care composition further comprises one or more oils in an amount less than 30% by weight of the vaginal care composition.

WW. The applicator, system, method, or kit according to any one of the preceding paragraphs, wherein the vaginal care composition is substantially free of one or more of the following: retinol, retinyl esters, retinaldehyde, peptides, ethanol, sunscreens, sensates, perfumes, pigments, and particulates having an average particle size greater than 125 microns.

XX. The applicator, system, method, or kit according to any one of the preceding paragraphs, wherein the applicator has a weight from about 10 g to about 125 g, preferably from about 25 g to about 100 g, more preferably from about 25 g to 75 g.

YY. The applicator, system, method, or kit according to any one of the preceding paragraphs, wherein the vaginal care composition has a viscosity from about 2,000 cps to about 200,000 cps, preferably from about 5,000 cps to about 150,000 cps, more preferably from about 20,000 cps to about 90,000 cps.

ZZ. A applicator, system, method, or kit according to any one of the preceding paragraphs for use in treating vaginal atrophy.

AAA. A applicator, system, method, or kit according to any one of the preceding paragraphs for use in treating vaginal dryness.

BBB. A applicator, system, method, or kit according to any one of the preceding paragraphs, wherein the vaginal dryness is from one or more of the group consisting of vaginitis, inflammation of the vagina due to thinning and shrinking of the tissues, sexual arousal disorder, menopause, drug induced vaginal dryness, dyspareunia, sexual pain disorder, pregnancy, hormone imbalance, anxiety and diabetes.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An applicator for treating vaginal dryness, comprising:
   a. a hand-held body for applying a composition to the vaginal introitus and/or external vaginal tissues, wherein the hand-held body comprises a proximal end, a cone-shaped insertion portion having a rounded tip opposite the proximal end, and a grippable portion, wherein the applicator has an overall length L1 and a maximum width $W_{max}$ and ratio of the overall length L1 to the maximum width $W_{max}$ is from about 1:2 to about 5:1, wherein the applicator tapers from the maximum width $W_{max}$ to the tip and from the maximum width $W_{max}$ to the proximal end.

2. The applicator according to claim 1, wherein the hand-held body comprises a cross-linked silicone rubber.

3. The applicator according to claim 1, wherein the composition is substantially free of an estrogen agent, a progesterone agent, or a combination thereof.

4. The applicator according to claim 1, wherein the hand-held body comprises a longitudinal axis.

5. The applicator according to claim 4, wherein the proximal end further comprises a substantially planar portion and wherein the applicator stands upright when placed on a flat surface.

6. The applicator according to claim 4, wherein the center of mass of the applicator is located along the longitudinal axis, in a lower one half of the body, or both.

7. The applicator according to claim 4, wherein the applicator has a rotational symmetry about the longitudinal axis thru a rotation of 45°, 90°, 135°, 180°, 225°, 270°, 315° or 360°.

8. The applicator according to claim 1, wherein the hand-held body is non-electrical.

9. The applicator according to claim 1, wherein the insertion portion further comprises a dosing indicator that delineates a dosing surface, wherein the dosing indicator is printed on the body, is in-molded with the body, or comprises a colored surface, a coating, text, a texture, or a graphic applied to or integrally formed with the body.

10. The applicator according to claim 1, wherein the grippable portion comprises a texture.

11. The applicator according to claim 1, wherein the hand-held body consists essentially of single material and wherein the single material is a cross-linked silicone rubber.

12. The applicator according to claim 1, wherein the applicator is not phallic shaped.

13. The applicator according to claim 1, wherein the applicator body exhibits one or more of:
   i) a Peak Force (Tip) from about 0.1N to about 40N; or
   ii) a Peak Force (Lateral Surface) from about 0.4N to about 90N; or
   iii) an absorbency less than 10%.

14. The applicator according to claim 1, wherein the composition comprises one or more oils selected from the group consisting of silicone oils and botanical oils.

15. The applicator according to claim 14, wherein the composition further comprises water in an amount greater than 60% by weight of the composition and wherein the one or more oils are present in an amount less than 30% by weight of the composition.

16. The applicator according to claim 1, wherein the composition is substantially free of one or more of the following: retinol, retinyl esters, retinaldehyde, peptides, ethanol, sunscreens, sensates, perfumes, pigments, and particulates having an average particle size greater than 125 microns.

17. The applicator according to claim 1, wherein the ratio of the overall length L1 to the maximum width $W_{max}$ is from about 1:2 to about 4:1.

18. A system for treating vaginal dryness, comprising:
   a. a vaginal care composition having a viscosity of from about 2,000 cps to about 200,000 cps;
   b. an applicator for treating vaginal dryness, the applicator comprising a hand-held body for applying the composition to the vaginal introitus and/or external vaginal tissues, wherein the hand-held body comprises a proximal end, a cone-shaped insertion portion having a rounded tip opposite the proximal end, and a grippable portion, wherein the insertion portion is shaped and configured to hold the composition, wherein the applicator has an overall length L1 and a maximum width $W_{max}$ and ratio of the overall length L1 to the maximum width $W_{max}$ is from about 1:2 to about 5:1.

19. A kit for treating vaginal dryness, comprising:
   a. a dispenser storing a composition;
   b. an applicator comprising a hand-held body for applying the composition to the vaginal introitus and/or external vaginal tissues, wherein the hand-held body comprises a proximal end, a cone-shaped insertion portion having a rounded tip opposite the proximal end, and a grippable portion, wherein the applicator is separate from the dispenser, wherein the applicator has an overall length L1 and a maximum width $W_{max}$ and ratio of the overall length L1 to the maximum width $W_{max}$ is from about 1:2 to about 5:1, and wherein the applicator tapers from the maximum width $W_{max}$ to the tip and from the maximum width $W_{max}$ to the proximal end.

* * * * *